United States Patent
Pender

(10) Patent No.: US 11,890,482 B2
(45) Date of Patent: Feb. 6, 2024

(54) MEDICAL DEVICE AND METHOD FOR ESTIMATING TIME BETWEEN VOLTAGE LEVELS OF A POWER SOURCE

(71) Applicant: Medtronic, Inc., Minneapolis, MN (US)

(72) Inventor: Jenna M.S. Pender, Saint Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 356 days.

(21) Appl. No.: 17/112,514

(22) Filed: Dec. 4, 2020

(65) Prior Publication Data
US 2021/0187305 A1   Jun. 24, 2021

Related U.S. Application Data

(60) Provisional application No. 62/951,095, filed on Dec. 20, 2019.

(51) Int. Cl.
| | | |
|---|---|---|
| A61N 1/37 | (2006.01) | |
| A61N 1/365 | (2006.01) | |
| A61N 1/372 | (2006.01) | |
| A61N 1/378 | (2006.01) | |
| A61N 1/02 | (2006.01) | |
| A61N 1/05 | (2006.01) | |

(52) U.S. Cl.
CPC .......... *A61N 1/3706* (2013.01); *A61N 1/025* (2013.01); *A61N 1/36521* (2013.01); *A61N 1/36542* (2013.01); *A61N 1/36585* (2013.01); *A61N 1/378* (2013.01); *A61N 1/37247* (2013.01); *A61N 1/0573* (2013.01)

(58) Field of Classification Search
CPC ............................. A61N 1/378; A61N 1/3708
See application file for complete search history.

(56) References Cited

U.S. PATENT DOCUMENTS

| | | |
|---|---|---|
| 5,031,616 A | 7/1991 | Mann et al. |
| 5,228,439 A | 7/1993 | Mann et al. |
| 5,447,525 A | 9/1995 | Powell et al. |
| 6,631,293 B2 | 10/2003 | Lyden |

(Continued)

FOREIGN PATENT DOCUMENTS

| | | |
|---|---|---|
| EP | 0972540 A3 | 12/2000 |
| WO | 2001034243 A1 | 5/2001 |
| WO | 2015084629 A1 | 6/2015 |

OTHER PUBLICATIONS (PCT/US2020/063858) PCT Notification of Transmittal of the International Search Report and the Written Opinion of the International Searching Authority, dated Mar. 5, 2021, 11 pages.

*Primary Examiner* — George R Evanisko

(57) ABSTRACT

A medical device system and method estimate a time from a first voltage of a power source of a medical device to a second voltage of the power source. The medical device includes a sensor coupled to the power source for generating a physiological signal. The medical device system determines a current drain from the power source required for generating the physiological signal and/or processing the physiological signal for detecting events from the physiological signal. A processor of the medical device system is configured to estimate the time from the first voltage of the power source until the second voltage based on at least the determined current drain.

27 Claims, 9 Drawing Sheets

(56) References Cited

U.S. PATENT DOCUMENTS

| | | | |
|---|---|---|---|
| 6,671,552 B2 * | 12/2003 | Merritt | A61N 1/3708 607/29 |
| 6,820,019 B1 | 11/2004 | Kelly et al. | |
| 8,209,010 B2 | 6/2012 | Ryu et al. | |
| 8,612,167 B2 | 12/2013 | Schmidt et al. | |
| 9,656,088 B2 | 5/2017 | Schilling et al. | |
| 10,286,214 B2 | 5/2019 | Demmer et al. | |
| 2009/0099625 A1 | 4/2009 | Crowley et al. | |
| 2015/0173655 A1 | 6/2015 | Demmer et al. | |
| 2019/0209847 A1 | 7/2019 | Younker et al. | |

* cited by examiner

MEDICAL DEVICE AND METHOD FOR ESTIMATING TIME BETWEEN VOLTAGE LEVELS OF A POWER SOURCE

REFERENCE TO RELATED APPLICATIONS

This application claims the benefit of U.S. Patent Application No. 62/951,095, filed provisionally on Dec. 20, 2019, incorporated herein by reference in its entirety.

TECHNICAL FIELD

This disclosure relates generally to medical devices having a depletable power source and a method for estimating the remaining time between two voltage levels of the power source.

BACKGROUND

A variety of medical devices for delivering a therapy and/or monitoring a physiological condition have been used clinically or proposed for clinical use in patients. Examples include medical devices that deliver therapy to and/or monitor conditions associated with the heart, muscles, nerves, brain, stomach or other organs or tissue of a patient. Some medical devices may employ one or more electrodes for the delivery of therapeutic electrical signals to such organs or tissues and/or one or more electrodes for sensing intrinsic electrical signals within the patient that are generated by such organs or tissue. Similarly, some medical devices may additionally or alternatively include one or more other sensors for sensing physiological parameters of a patient for monitoring a medical condition.

For example, some medical devices may function as cardiac pacemakers or cardioverter-defibrillators that provide therapeutic electrical signals to the heart. The therapeutic electrical signals may include pulses for pacing or shocks for cardioversion or defibrillation. In some examples, a medical device may sense signals from the patient for use in controlling the delivery of the therapeutic electrical signals. For instance, intrinsic cardiac electrical signals attendant to depolarizations of the heart may be sensed for controlling delivery of therapeutic signals to the heart based on the sensed intrinsic signals. Upon detection of an abnormal rhythm, such as bradycardia, tachycardia, or fibrillation, an appropriate therapeutic electrical stimulation pulse or pulses may be delivered to restore or promote a relatively more normal heart rhythm. For example, in some cases, an implanted medical device may deliver pacing stimulation to the heart of the patient upon detecting tachycardia or bradycardia, and/or deliver cardioversion or defibrillation shocks to the heart upon detecting fibrillation. A rate responsive pacemaker may sense a signal from the patient that is correlated to the patient's physical activity to control a rate of pacing the heart.

Implantable medical devices are typically powered by one or more internal batteries, which are depleted over time as the battery capacity is used to power various electronic components and processors that perform the medical device functions, such as sensing signals from the patient by one or more sensors and/or generating and delivering a therapy to the patient.

SUMMARY

The techniques of this disclosure generally relate to estimating a time remaining between two voltage points of a power source of a medical device. The medical device may be an implantable medical device (IMD), such as an implantable pulse generator (IPG) configured to deliver therapeutic electrical stimulation pulses powered by one or more batteries. The IMD may be a cardiac pacemaker, implantable cardioverter defibrillator (ICD), or provide therapeutic electrical stimulation to muscle, nerve or brain as examples. In other examples, the IMD may be a medical monitor configured to sense physiological signals without therapy delivery capabilities.

A medical device operating according to techniques disclosed herein determines an estimated time remaining between two voltages of the medical device power supply by determining a current drain required to perform medical device functions that may vary over time. The determined current drain may include estimates of a sensor operation current drain, a processing burden current drain and a therapy delivery current drain. Each of these current drains may be estimated based on the historical function of the medical device since being put into service for the patient, e.g., from the time of implantation of an IMD.

In one example, a medical device system includes a power source, a sensor coupled to the power source for generating a physiological signal, a control circuit coupled to the power source and the sensor, and a processor. The control circuit is configured to operate in an operating mode that includes detecting an event from the physiological signal. The processor is configured to determine a current drain from the power source required for operating in the operating mode. The current drain is associated with electrical current required from the power source for at least one of generating the physiological signal or detecting the event from the physiological signal. The processor is further configured to determine an estimated time from a first voltage of the power source until a second voltage of the power source based on the current drain and a power source capacity difference. The first voltage of the power source corresponds to a first power source capacity, and the second voltage corresponds to a second power source capacity less than the first power source capacity. The power source capacity difference is the difference between the first power source capacity and the second power source capacity. The processor is configured to generate an output based on the estimated time. A memory may be configured to store data related to the estimated time in response to the generated output.

In another example, a method includes generating a physiological signal by a sensor, detecting an event from the physiological signal for use in operating in an operating mode of a medical device, and determining a current drain from a power source required for operating in the operating mode. The current drain is associated with electrical current required from the power source for at least one of: generating the physiological signal or detecting the event from the physiological signal. The method further includes determining an estimated time from a first voltage of the power source until a second voltage of the power source based on the current drain and a power source capacity difference. The first voltage of the power source corresponds to a first power source capacity, and the second voltage corresponds to a second power source capacity less than the first power source capacity. The power source capacity difference is the difference between the first power source capacity and the second power source capacity. The method further includes generating an output based on the estimated time and may include storing data related to the estimated time in response to the generated output.

In yet another example, a non-transitory computer readable medium storing a set of instructions that, when executed by processing circuitry of a medical device system, cause the medical device system to generate a physiological signal by a sensor, detect an event from the physiological signal for use in operating in an operating mode of the medical device system, and determine a current drain from a power source required for operating in the operating mode. The current drain is associated with electrical current required from the power source for at least one of: generating the physiological signal or detecting the event from the physiological signal. The instructions further cause the medical device system to determine an estimated time from a first voltage of the power source until a second voltage of the power source based on the current drain and a power source capacity difference. The first voltage of the power source corresponds to a first power source capacity, and the second voltage corresponds to a second power source capacity less than the first power source capacity. The power source capacity difference is the difference between the first power source capacity and the second power source capacity. The instructions further cause the system to generate an output based on the estimated time and may cause a memory of the system to store data relating to the estimated time in response to the generated output.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
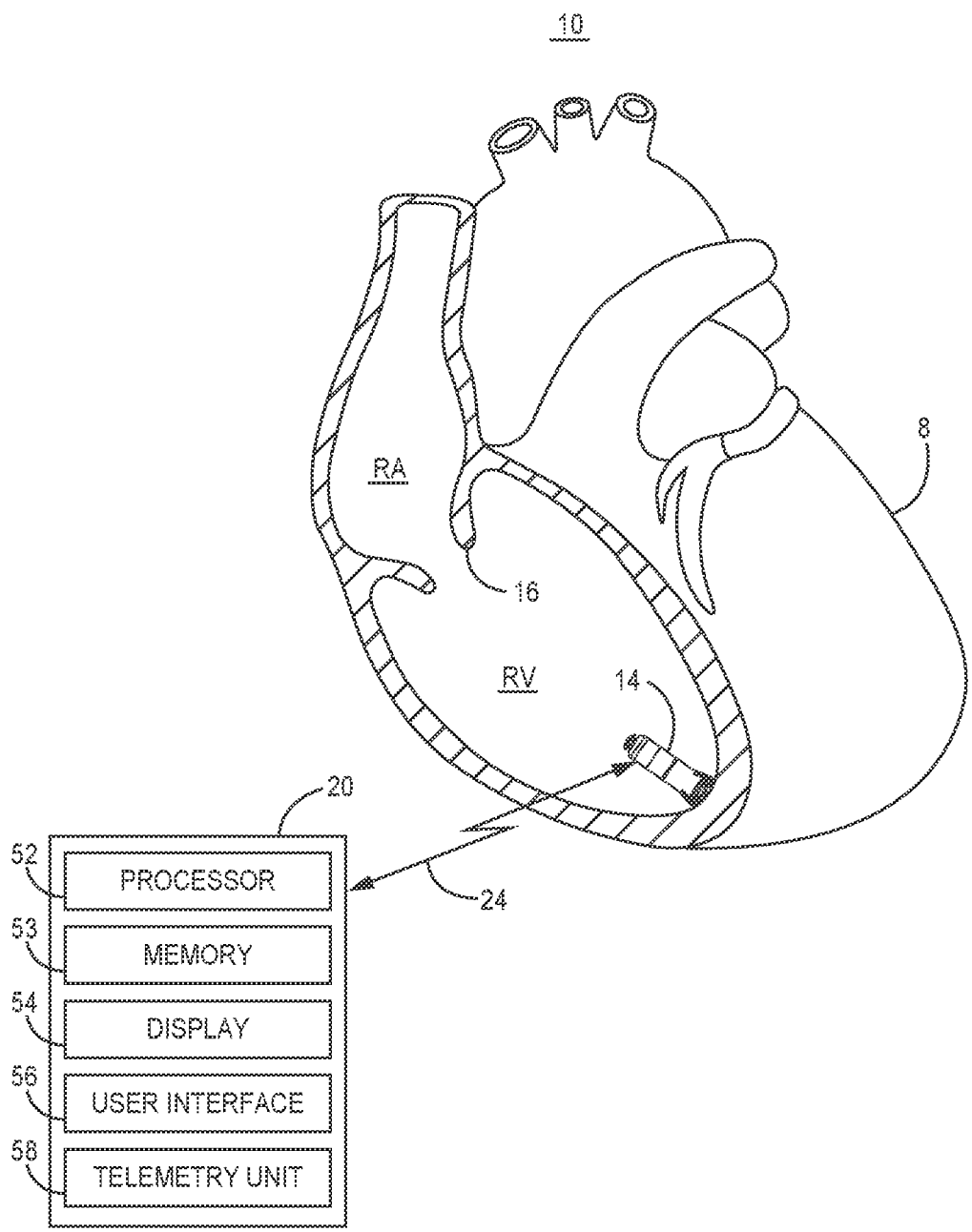
FIG. 1 is a conceptual diagram illustrating an IMD system including a battery-powered IMD that may be used to sense signals from a patient and deliver therapeutic electrical stimulation therapy.

In general, this disclosure is directed to medical devices and techniques for determining an estimated longevity of a power source of the medical device between two voltage levels. The term "longevity" as used herein refers to the time, e.g., in years, weeks, days, hours, or minutes, between two voltage levels of a power source of the medical device.

By estimating the longevity or time to a predetermined voltage level from a current voltage level, the remaining useful life of the medical may be estimated and/or a recommended time for recharging or replacing the power source of the medical device (or replacing the medical device itself) may be reported, which may precede the end of the functional life of the medical device. The medical device may be an 1 MB but is not necessarily an implantable device. For instance, the medical device may be a wearable device or a bedside or remote monitor that is battery powered. In various examples, a medical device performing the techniques disclosed herein includes an internal or portable power source which is depleted over time as it powers the medical device functions. The power source may include one or more rechargeable or non-rechargeable batteries, as examples.

As disclosed herein, a technique for estimating the power source longevity includes determining an estimated current drain from the power source required for performing various device functions that may vary over time. In some examples, the estimated current drain may include a current drain required for operating a physiological sensor and/or processing the physiological signal produced by the sensor. A monitoring or therapy delivery function may vary over time as patient need and/or the medical device operating mode changes over time, due to automatic or manual adjustments for example. As a result, the demand for current from the medical device power source by one or more electronic components, such as a therapy delivery circuit, a sensor circuit, or a processing circuit, may vary over time. As such, a longevity estimate may be determined by taking into account estimations of current drain required to perform device functions that may vary over time based at least in part on historical functional data that may be stored by the medical device.

For example, the longevity estimation may require determining a current drain from a medical device power source that is required for operating in a particular therapy delivery mode. The therapy delivery mode may be one operating mode of the medical device for controlling and generating a therapy that is delivered to the patient. The therapy delivery mode may require generating a physiological signal by a sensor for analysis and use in controlling the therapy delivery and timing. Accordingly, estimating the longevity may include determining the current drain associated with operating a sensor to generate the physiological signal by the sensor and/or a processing burden required by a processor to analyze the physiological signal for use in controlling the therapy delivery. Determining the estimated longevity may further include estimating current drain required for generating and delivering a therapy, e.g., the current drain required for generating electrical stimulation pulses such as cardiac pacing pulses. Multiple components of an estimated total current drain, e.g., a processing burden current drain, a sensor operation current drain, and/or a therapy delivery current drain that may each change dynamically over time, may be determined for use in estimating power source longevity between two voltages of the medical device power source. The total current drain may also take into account a static current drain that is required to perform medical device functions that may be relatively static or constant over the functional life of the medical device. By determining current drain estimates for dynamic monitoring and/or therapy delivery functions of a medical device, longevity estimates may be more accurate thereby improving the medical device by providing more reliable notifications or warnings to a user, clinician or caregiver as a power source is being depleted.

FIG. 1 is a conceptual diagram illustrating an IMD system 10 that may be used to sense signals from a patient and deliver therapeutic electrical stimulation therapy. IMD system 10 includes an IMD 14, which may be configured for wireless communication with an external device 20 in some examples. IMD 14 is shown as a leadless cardiac pacemaker as one example of a medical device that may be configured to estimate power source longevity according to the techniques disclosed herein. IMD 14 may be a transcatheter intracardiac pacemaker which is adapted for implantation wholly within a heart chamber, e.g., wholly within the right ventricle (RV) as shown, wholly within the left ventricle (LV), or wholly within an atrial chamber of heart 8. IMD 14 may be reduced in size compared to subcutaneously implanted pacemakers or other IMDs and may be generally cylindrical in shape to enable transvenous implantation via a delivery catheter. IMD 14 is shown positioned in the RV, along an endocardial wall, e.g., near the RV apex though various positions within or on heart 8 or other implant sites within the patient's body are possible.

IMD 14 is capable of producing electrical stimulation pulses, e.g., pacing pulses, delivered to heart 8 via one or more electrodes on the outer housing of the IMD 14. For example, IMD 14 may be configured to deliver ventricular pacing pulses and sense a cardiac electrical signal using housing based electrodes for producing an intracardiac electrogram (EGM) signal. The cardiac electrical signals may be sensed using the housing based electrodes that are also used to deliver pacing pulses to the RV. As described below, IMD 14 may additionally include a physiological sensor other than electrodes that is powered by the IMD power source for generating a physiological signal other than the EGM signal. The physiological signal may be analyzed by processing circuitry enclosed by a housing of IMD 14 for use in controlling cardiac pacing therapy. In one example, the physiological signal is a motion signal that includes cardiac motion for detecting cardiac mechanical events as described below.

IMD 14 may be configured to control the delivery of cardiac pacing pulses to the heart 8 in a manner that promotes synchrony between atrial activation and ventricular activation, e.g., by maintaining a target atrioventricular (AV) interval between atrial events and ventricular pacing pulses. That is, IMD 14 controls pacing pulse delivery to maintain a desired AV interval between atrial contractions corresponding to atrial systole and ventricular pacing pulses delivered to cause ventricular depolarization and ventricular systole.

In some examples, atrial systolic events producing the active ventricular filling phase may be detected by IMD 14 implanted in a ventricular chamber. The atrial systolic events may be detected from a motion sensor such as an accelerometer enclosed by the housing of IMD 14. The motion signal produced by an accelerometer implanted within a ventricular chamber, which may be referred to as an "intraventricular motion signal," includes motion signals caused by ventricular and atrial events. For example, acceleration of blood flowing into the RV through the tricuspid valve 16 between the RA and RV caused by atrial systole, and referred to as the "atrial kick," may be detected by IMD 14 from the signal produced by an accelerometer included in IMD 14. Other motion signals may be detected by IMD 14, such as motion caused by ventricular contraction and/or passive ventricular filling as well as motion due to patient physical activity. The accelerometer (or other type of motion sensor) may be configured to produce a patient activity signal correlated to physical activity level of the patient.

In some examples, IMD 14 may be configured to operate in at least two different therapy delivery modes. One therapy delivery mode may be an atrial synchronized ventricular pacing mode in which atrial systolic events are sensed from an acceleration signal produced by an accelerometer included in IMD 14, and a ventricular pacing pulse is generated in response to a sensed atrial systolic event. Another therapy delivery mode may be a non-atrial tracking ventricular pacing mode, which does not require atrial systolic event sensing from the acceleration signal for controlling the timing of ventricular pacing pulses on a beat-by-beat basis. Ventricular pacing pulses may be delivered according to a programmed lower pacing rate, which may be adjustable to temporary pacing rates set based on patient physical activity level determined from the accelerometer signal. In the non-atrial tracking ventricular pacing mode, IMD 14 may be configured to provide rate responsive pacing by adjusting the pacing rate delivered to heart 8. For instance, as the patient physical activity level increases, the pacing rate is increased to provide appropriate metabolic support.

The current drain on the IMD power source may be different for the two different therapy delivery modes since one mode may require increased current drain compared to the other therapy delivery mode. In the example of atrial tracking and non-atrial ventricular pacing modes, the atrial tracking therapy delivery mode requires greater current for dual chamber sensing than the non-atrial tracking ventricular pacing mode, which does not require dual chamber sensing. The dual chamber sensing required during the atrial tracking pacing mode requires current drain for operating the accelerometer on a continuous or beat-by-beat basis for detecting atrial systolic events and for operating a processor for analyzing the acceleration signal for detecting the atrial systolic events. In other examples, IMD 14 may have a single therapy delivery mode however the rate of generating pacing pulses may be variable over time and/or the current drain required for operating a sensor for patient monitoring purposes may be variable over time. The longevity estimate techniques disclosed herein account for dynamic changes in power source current drain, which may depend on the sensing operating mode, the therapy delivery operating mode and/or other factors.

IMD 14 may be capable of bidirectional wireless communication with an external device 20 for programming IMD operating parameters such as sensing and pacing control parameters. Aspects of external device 20 may generally correspond to the external programming/monitoring unit disclosed in U.S. Pat. No. 5,507,782 (Kieval, et al.), hereby incorporated herein by reference in its entirety. External device 20 is often referred to as a "programmer" because it is typically used by a physician, technician, nurse, clinician or other qualified user for programming operating parameters in IMD 14. External device 20 may be located in a clinic, hospital or other medical facility. External device 20 may alternatively be embodied as a home monitor or a handheld device that may be used in a medical facility, in the patient's home, or another location.

External device 20 may include a processor 52, memory 53, display 54, user interface 56 and telemetry unit 58. Processor 52 controls external device operations and processes data and signals received from IMD 14. Display unit 54, which may include a graphical user interface, displays data and other information to a user for reviewing IMD operation and programmed parameters as well as cardiac electrical signals and acceleration or other sensor signals retrieved from IMD 14. Display unit 54 may generate a display of data and information relating to IMD functions to a user for reviewing IMD operation and programmed parameters as well as cardiac electrical signals, cardiac motion signals or other physiological data that may be acquired by IMD 14 and transmitted to external device 20 during an interrogation session.

User interface 56 may include a mouse, touch screen, key pad or the like to enable a user to interact with external device 20 to initiate a telemetry session with IMD 14 for retrieving data from and/or transmitting data to IMD 14, including programmable parameters for controlling cardiac event sensing and therapy delivery. Telemetry unit 58 includes a transceiver and antenna configured for bidirectional communication with a telemetry circuit included in IMD 14 and is configured to operate in conjunction with processor 52 for sending and receiving data relating to pacemaker functions via communication link 24.

In some examples, external device processor 52 may execute operations disclosed herein for determining current drain and/or estimating IMD power source longevity using data retrieved from IMD 14 via communication link 24. Processor 52 may cause display unit 54 to generate an output stored in memory 53 and used to display data relating to IMD power source longevity, such as measured power source voltage, estimated longevity, historical sensor operation and/or therapy delivery related data used to estimate the longevity, and/or one or more notifications related to replacement or recharging time recommendations. Display unit 54 may be a graphical user interface that enables a user to interact with the display, e.g., for selecting various displays or information for viewing. In some examples, a user may enter one or more programmable parameter settings used to control sensor operation and therapy delivery for estimating comparative longevities. For instance, processing circuitry included in IMD 14 and/or processor 52 may determine an estimated longevity based on currently programmed sensing and therapy delivery control parameters and actual historical data.

In some examples, processor 52 may be configured to determine multiple comparative estimated IMD power source longevities stored in memory 53 and cause display unit 54 to generate a display of the results. For example, a user may enter one or more alternative programmable settings for sensing and/or therapy delivery control parameters via user interface 56. Processor 52 may determine one or more alternative estimated longevities based on the alternative settings for comparison to the longevity that is estimated based on current, actual programmed control parameters and actual historical IMD operational data. Processor 52 may cause display unit 54 to generate a comparative display of the actual longevity estimate and the alternative longevity estimate(s) based one or more programmable control parameter being reprogrammed to the user-entered alternative setting(s). Based on this comparative display, a user may select to change one or more programmable sensing or therapy delivery control parameters based on patient need with the knowledge of how the IMD power supply longevity is expected to be affected. Any control parameter programming changes may be transmitted back to IMD 14 via communication link 24. In some cases, a programming change may increase the estimated IMD power source longevity, and in other instances the programming change may decrease the estimated longevity as an acceptable trade-off for improving patient monitoring or potential therapeutic benefit of a delivered therapy.

Communication link 24 may be established between IMD 14 and external device 20 using a radio frequency (RF) link such as BLUETOOTH®, Wi-Fi, or Medical Implant Communication Service (MICS) or other RF or communication frequency bandwidth or communication protocols. Data stored or acquired by IMD 14, including physiological signals or associated data derived therefrom, results of device diagnostics, and histories of detected rhythm episodes and delivered therapies, as well as estimated longevity and/or data that may be used by external device 20 for computing an estimated longevity may be retrieved from IMD 14 by external device 20 following an interrogation command. In some examples, external device 20 may include a programming head that is placed proximate IMD 14 to establish and maintain a communication link 24, and in other examples external device 20 and IMD 14 may be configured to communicate using a distance telemetry algorithm and circuitry that does not require the use of a programming head and does not require user intervention to maintain a communication link.

In some examples, a user may interact with external device 20 to transmit a command via communication link 24 to perform an IMD power source longevity estimate and return the estimated longevity and/or data used to compute the estimated longevity. In other examples, during any established communication session when an estimated longevity is available, e.g., stored in IMD memory, IMD 14 may transmit a notification to external device 20 relating to the estimated longevity of the IMD power source, which may include an estimated number of days (or other units of time) remaining to a specified voltage level or a recommended replacement time or end-of-service notification as described below.

It is contemplated that external device 20 may be in wired or wireless connection to a communications network via a telemetry circuit that includes a transceiver and antenna or via a hardwired communication line for transferring data to a centralized database or computer to allow remote management of the patient. Remote patient management systems including a centralized patient database may be configured to utilize the presently disclosed techniques to enable a clinician to review programmed parameters in IMD 14 and data retrieved from IMD 14, including data and notifications relating to the estimated longevity of the IMD power source.

Figure 2:
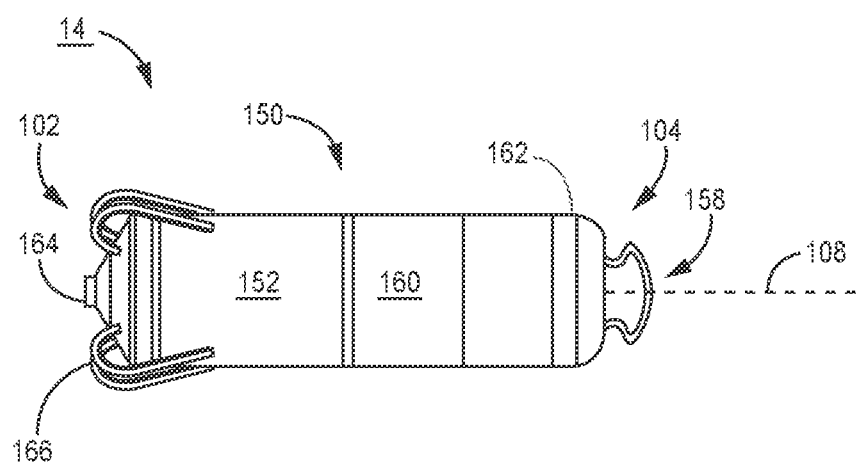
FIG. 2 is a conceptual diagram of the IMD shown in FIG. 1.

FIG. 2 is a conceptual diagram of IMD 14 shown in FIG. 1 according to one example. IMD 14 includes a housing 150 that encloses a power source and internal device circuitry. IMD 14 includes electrodes 162 and 164 spaced apart along the housing 150 for sensing cardiac electrical signals and delivering pacing pulses. Electrode 164 is shown as a tip electrode extending from a distal end 102 of IMD 14, and electrode 162 is shown as a ring electrode along a midportion of housing 150, for example adjacent proximal end 104. Distal end 102 is referred to as "distal" in that it is expected to be the leading end as IMD 14 is advanced through a delivery tool, such as a catheter, and placed against a targeted pacing site.

Electrodes 162 and 164 form an anode and cathode pair for bipolar cardiac pacing and sensing. In alternative embodiments, IMD 14 may include two or more ring electrodes, two tip electrodes, and/or other types of electrodes exposed along housing 150 for delivering electrical stimulation to the patient's heart and sensing cardiac electrical signals. Electrodes 162 and 164 may be, without limitation, titanium, platinum, iridium or alloys thereof and may include a low polarizing coating, such as titanium nitride, iridium oxide, ruthenium oxide, platinum black, among others. Electrodes 162 and 164 may be positioned at locations along IMD 14 other than the locations shown. While IMD 14 is shown as a leadless pacemaker having housing-based electrodes, in other examples IMD 14 may be configured to be coupled to one or more medical electrical leads carrying one or more electrodes and/or other sensors for sensing cardiac or other physiological signals.

Housing 150 is formed from a biocompatible material, such as a stainless steel or titanium alloy. In some examples, the housing 150 may include an insulating coating. Examples of insulating coatings include parylene, urethane, PEEK, or polyimide, among others. The entirety of the housing 150 may be insulated, but only electrodes 162 and 164 uninsulated. Electrode 164 may serve as a cathode electrode and be coupled to internal circuitry, e.g., a pacing pulse generator and cardiac electrical signal sensing circuitry, enclosed by housing 150 via an electrical feedthrough crossing housing 150. Electrode 162 may be formed as a conductive portion of housing 150 defining a ring electrode that is electrically isolated from the other portions of the housing 150 as generally shown in FIG. 2. In other examples, the entire periphery of the housing 150 may function as an electrode that is electrically isolated from tip electrode 164, instead of providing a localized ring electrode such as anode electrode 162. Electrode 162 formed along an electrically conductive portion of housing 150 serves as a return anode during pacing and sensing with cathode tip electrode 164.

The housing 150 may include a control electronics subassembly 152, which houses the electronics for sensing cardiac signals, producing pacing pulses and controlling therapy delivery and other functions of IMD 14 as described below in conjunction with FIG. 3. A motion sensor may be implemented as a multi-axis accelerometer enclosed within housing 150 in some examples. The accelerometer provides a signal to a processor included in control electronics subassembly 152 for signal processing and analysis for detecting atrial systolic events, e.g., for use in controlling the timing of ventricular pacing pulses synchronized to atrial events, and/or detecting patient physical activity, e.g., for use in controlling a rate responsive ventricular pacing rate.

The accelerometer may be a three-dimensional accelerometer. In some examples, the accelerometer may have one "longitudinal" axis that is parallel to or aligned with the longitudinal axis 108 of IMD 14 and two orthogonal axes that extend in radial directions relative to the longitudinal axis 108. Each axis of a single or multi-dimensional accelerometer may be defined by a piezoelectric element, microelectrical mechanical system (MEMS) device or other sensor element capable of producing an electrical signal in response to changes in acceleration imparted on the sensor element, e.g., by converting the acceleration to a force or displacement that is converted to the electrical signal. In a multi-dimensional accelerometer, the sensor elements may be arranged orthogonally or non-orthogonally. Each sensor element or "axis" may produce an acceleration vector signal corresponding to a vector aligned with the direction of the axis of the sensor element.

In some cases one, two or all three acceleration vector signals produced by a three dimensional accelerometer may be selected for use in detecting cardiac mechanical events, e.g., atrial systolic events for controlling atrial-synchronized ventricular pacing delivered by IMD 14. The number of axes of a multi-dimensional accelerometer selected for monitoring motion will impact the current drain of the IMD power source. As such, the techniques disclosed herein for estimating longevity to a specified power source voltage level may take into account the number of accelerometer axes selected for monitoring cardiac motion and/or patient physical activity and the accumulated time, which may be determined as a percentage of time since implantation of IMD 14, that each axis of the accelerometer is powered on for producing a vector signal.

Housing 150 further includes a battery subassembly 160, which is the IMD power source providing power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety. Control circuitry included in control electronics subassembly 152 is configured to measure the voltage of the battery (or batteries) included in battery subassembly 160. As described below, when a predetermined voltage is reached that corresponds to a known remaining capacity of the power source (e.g., the one or more batteries included in battery subassembly 160), the control circuitry may determine an estimated longevity until a second specified voltage is reached, e.g., a voltage that is specified as an end of service (EOS) voltage, below which the battery capacity is insufficient to power the circuitry of control electronics subassembly 152 for performing normal IMD operations.

IMD 14 may include a set of fixation tines 166 to secure IMD 14 to patient tissue, e.g., by actively engaging with the ventricular endocardium and/or interacting with the ventricular trabeculae. Fixation tines 166 are configured to anchor IMD 14 to position electrode 164 in operative proximity to a targeted tissue for delivering therapeutic electrical stimulation pulses. Numerous types of active and/or passive fixation members may be employed for anchoring or stabilizing IMD 14 in an implant position. IMD 14 may optionally include a delivery tool interface 158. Delivery tool interface 158 may be located at the proximal end 104 of IMD 14 and is configured to connect to a delivery device, such as a catheter, used to position IMD 14 at an implant location during an implantation procedure, for example within a heart chamber.

The example of IMD 14 configured as a leadless, intracardiac pacemaker and capable of determining longevity estimates according to the techniques disclosed herein is illustrative in nature. It is to be understood that the disclosed techniques may be implemented in a wide variety of implantable and non-implantable medical device having a depletable power supply, e.g., one or more rechargeable or non-rechargeable batteries. The disclosed techniques may be used for estimating time between two predetermined voltage levels of a depletable power supply of any medical device having a physiological signal sensor and/or therapy delivery capabilities that require electrical current from the depletable power supply. In some examples, the estimated time or longevity is from a predetermined voltage level associated with a known power supply capacity until a second voltage level associated with a second, lower known power supply capacity. The second, lower voltage and power supply capacity may be an end-of service voltage at which remaining capacity is insufficient to power the medical device functions. In this case the longevity is an estimate of the remaining functional life of the power supply of the medical device. In other examples the estimated time is from a predetermined voltage until another pre-determined voltage level (and known battery capacity) is reached, which may correspond to a recommended voltage level at which the replacement or recharging of the power supply may be recommended or required.

Various medical devices that may implement aspects of the disclosed techniques may include cardiac pacemakers, implantable cardioverter defibrillators, neurological stimulators, muscle stimulators, drug pumps, cardiac monitors, blood pressure monitors or the like. Such devices may be leadless devices having housing based electrodes, as generally shown in FIG. 2, or devices configured to be coupled to one or more medical electrical leads carrying electrodes and/or other sensors. Furthermore, while the illustrative examples presented herein refer to a single chamber pacemaker with dual chamber sensing capabilities, it is to be understood that the techniques disclosed herein may be implemented in any single chamber, dual chamber or multi-chamber pacemaker or ICD.

Figure 3:
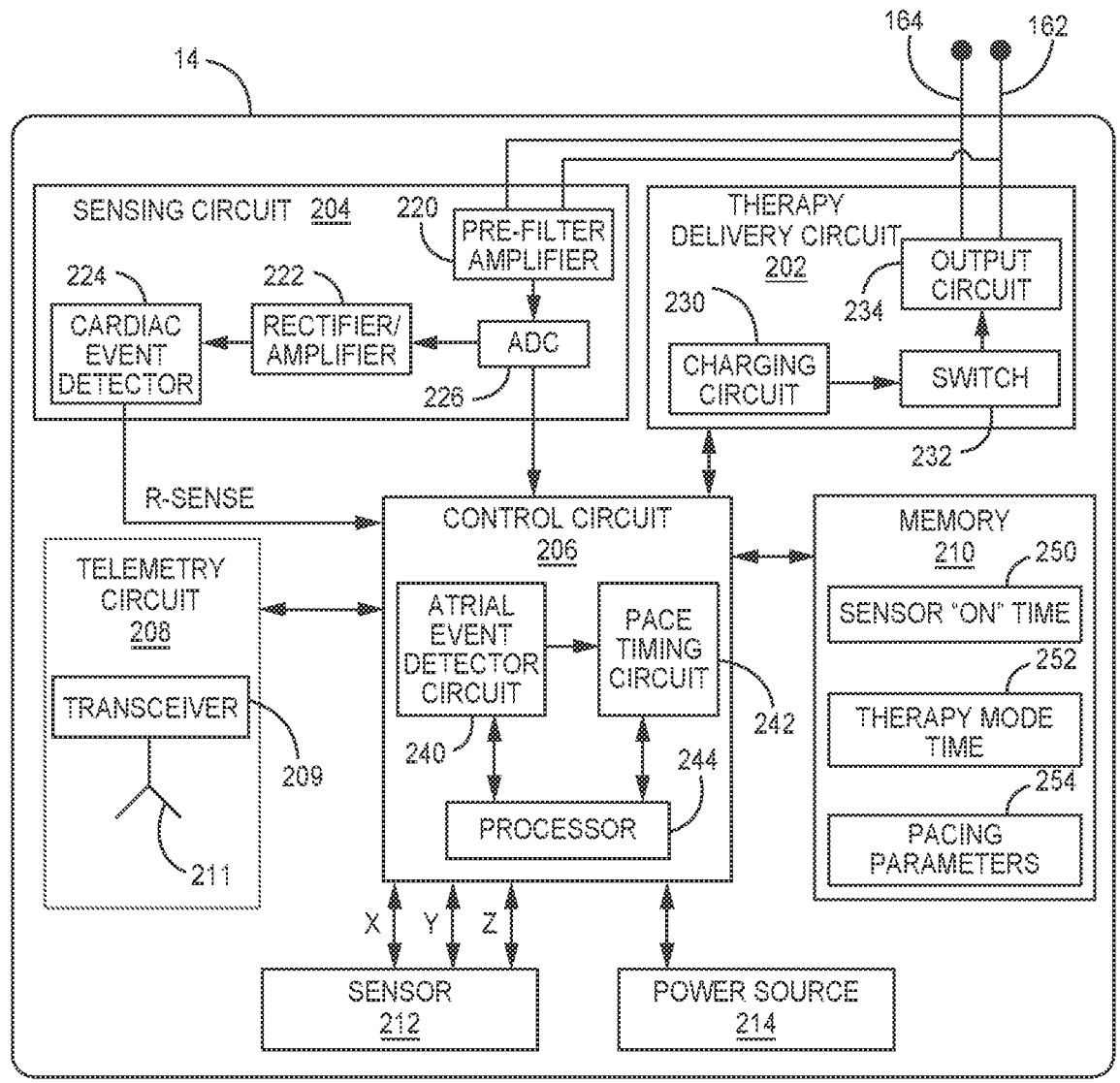
FIG. 3 is a schematic diagram of an example configuration of the IMD shown in FIG. 1.

FIG. 3 is a schematic diagram of an example configuration of IMD 14 shown in FIG. 1. IMD 14 may include a therapy delivery circuit 202, a cardiac electrical signal sensing circuit 204, a control circuit 206, memory 210, telemetry circuit 208, physiological sensor 212 and a power source 214. The various circuits represented in FIG. 3 may be combined on one or more integrated circuit boards which include a specific integrated circuit (ASIC), an electronic circuit, a processor (shared, dedicated, or group) and memory that execute one or more software or firmware programs, a combinational logic circuit, state machine or other suitable components that provide the described functionality.

Power source 214 provides power to control circuit 206 and each of the other circuits and components of IMD 14 as required to perform the functionality attributed to IMD 14. Power source 214 may include one or more energy storage devices, such as one or more rechargeable or non-rechargeable batteries. Power source 214 may correspond to a battery subassembly, such as battery subassembly 160 coupled to a control electronics subassembly 152 in which the other circuitry and components may reside. However, the architecture of power source 214 and other medical circuitry may vary between medical devices and depend on the particular medical device size, power requirements, shape, etc. The connections between power source 214 and other IMD circuits and components are not all shown in FIG. 3 for the sake of clarity but are to be understood from the general block diagram of FIG. 3. For example, power source 214 may provide power as needed to charging and switching circuitry included in therapy delivery circuit 202; to amplifiers, analog to digital converter (ADC) 226 and other components of cardiac electrical signal sensing circuit 204; to telemetry circuit 208; to memory 210, and to sensor 212 under the control of control circuit 206.

Sensor 212 includes an accelerometer in the examples described herein. Sensor 212 produces an electrical signal correlated to motion or vibration of sensor 212 (and IMD 14), e.g., when subjected to flowing blood and cardiac motion in an intracardiac or other implant location. Sensor 212 is not limited to being an accelerometer, however, and other physiological sensors may be utilized in a medical device for sensing physiological signals from the patient for detecting events and controlling therapy delivery or for monitoring for a physiological condition. In the examples presented herein, however, sensor 212 is provided as an accelerometer for generating acceleration signals due to cardiac events, e.g., contraction and relaxation of the heart chambers, and may include acceleration signals due to patient physical activity or other body motion.

Sensor 212 may include a multi-axis accelerometer, e.g., a two-dimensional or three-dimensional accelerometer, with each accelerometer axis individually selectable for providing a signal (designated as X-, Y-, or Z-axis signals in FIG. 3) that may be analyzed individually or in combination with one or more other accelerometer axis signals for detecting cardiac mechanical events and/or for monitoring patient physical activity. Sensor 212 may include one or more filter, amplifier, rectifier, analog-to-digital converter (ADC) and/or other components for producing an acceleration signal from each accelerometer axis that is passed to control circuit 206. For example, each axis of a multi-axis accelerometer may produce an acceleration vector signal corresponding to acceleration along the respective axis. Each individual axis signal may be filtered by a high pass filter, e.g., a 10 Hz high pass filter. The filtered signal may be digitized by an ADC and rectified for use by control circuit 206 for detecting cardiac events. The high pass filter may be lowered (e.g., to 5 Hz) if needed to detect atrial signals that have lower frequency content in some examples. In other examples, each accelerometer axis signal of sensor 212 is filtered by a low pass filter, e.g., a 30 Hz low pass filter, with or without high pass filtering.

Each accelerometer axis, which may sometimes be referred to as a "channel" produces an acceleration vector signal that is passed to signal processing circuitry, for example for generating a filtered, digitized acceleration vector signal. Each accelerometer axis may be individually selectable by control circuit 206. For example, power control signals may be passed by control circuit 206 to sensor 212 to enable power source 214 to selectively power each accelerometer axis for generating an acceleration vector signal. One, two or all three accelerometer axes may be selected for generating acceleration vectors signals (e.g., X, Y, or Z signals) that are used by control circuit 206 individually or in combination for detecting cardiac events used in controlling a rate or frequency of therapy delivered by therapy delivery circuit 202.

Furthermore, control circuit 206 may select one or more accelerometer axis signals for sensing other types of events or motion. For example, one or more accelerometer axis signals may be selected individually or in combination as a patient physical activity signal used by control circuit 206 to determine a patient activity metric. Control circuit 206 may use the patient activity metric to control a rate of therapy delivered by therapy delivery circuit 202, e.g., to provide rate responsive cardiac pacing.

One example of an accelerometer for use in implantable medical devices that may be implemented in conjunction with the techniques disclosed herein is generally disclosed in U.S. Pat. No. 5,885,471 (Ruben, et al.), incorporated herein by reference in its entirety. An implantable medical device arrangement including a piezoelectric accelerometer for detecting patient motion is disclosed, for example, in U.S. Pat. No. 4,485,813 (Anderson, et al.) and U.S. Pat. No. 5,052,388 (Sivula, et al.), both of which patents are hereby incorporated by reference herein in their entirety. Examples of three-dimensional accelerometers that may be implemented in IMD 14 and used for detecting cardiac mechanical events using the presently disclosed techniques are generally described in U.S. Pat. No. 5,593,431 (Sheldon) and U.S. Pat. No. 6,044,297 (Sheldon), both of which are incorporated herein by reference in their entirety. Other accelerometer designs may be used for producing an electrical signal that is correlated to acceleration imparted on IMD 14 due to cardiac motion and due to patient physical activity.

Cardiac electrical signal sensing circuit 204 is configured to receive a cardiac electrical signal via electrodes 162 and 164 by a pre-filter and amplifier circuit 220. Pre-filter and amplifier circuit 220 may include a high pass filter to remove DC offset, e.g., a 2.5 to 5 Hz high pass filter, or a wideband filter having a passband of 2.5 Hz to 100 Hz to remove DC offset and high frequency noise. Pre-filter and amplifier circuit 220 may further include an amplifier to amplify the "raw" cardiac electrical signal passed to analog-to-digital converter (ADC) 226. ADC 226 may pass a multi-bit, digital EGM signal to control circuit 206 for use by control circuit 206 in identifying ventricular electrical events (e.g., R-waves or T-waves attendant to ventricular myocardial depolarization and repolarization, respectively) and/or atrial electrical events, e.g., P-waves attendant to atrial myocardial depolarization. Identification of cardiac electrical events may be used in algorithms for establishing atrial systolic event sensing control parameters applied to an acceleration signal from sensor 212.

The digital signal from ADC 226 may be passed to rectifier and amplifier circuit 222, which may include a rectifier, bandpass filter, and amplifier for passing a cardiac signal to cardiac event detector 224. Cardiac event detector 224 may include a sense amplifier or other detection circuitry that compares the incoming rectified, cardiac electrical signal to a cardiac event sensing threshold, e.g., to an R-wave sensing threshold, which may be an auto-adjusting threshold. When the incoming signal crosses the R-wave sensing threshold, the cardiac event detector 224 produces an R-wave sensed event signal (R-sense) that is passed to control circuit 206. In other examples, cardiac event detector 224 may receive the digital output of ADC 226 for detecting R-waves by a comparator, morphological signal analysis of the digital EGM signal or other R-wave detection techniques. Control circuit 206 may provide sensing control signals to cardiac electrical signal sensing circuit 204, e.g., R-wave sensing threshold, sensitivity, and various blanking and refractory intervals applied to the cardiac electrical signal for controlling R-wave sensing. R-wave sensed event signals passed from cardiac event detector 224 to control circuit 206 may be used for scheduling ventricular pacing pulses and for use in identifying the timing of ventricular electrical events in algorithms performed for detecting atrial systolic events from a signal received from sensor 212.

Control circuit 206 is shown including an atrial event detector circuit 240, pace timing circuit 242, and processor 244. Control circuit 206 may receive R-wave sensed event signals and/or digital cardiac electrical signals from cardiac electrical signal sensing circuit 204 for use in detecting and confirming cardiac events and controlling ventricular pacing. For example, R-wave sensed event signals may be passed to pace timing circuit 242 for inhibiting scheduled ventricular pacing pulses or scheduling ventricular pacing pulses when IMD 14 is operating in a non-atrial tracking ventricular pacing mode, e.g., a VDI or VVI pacing mode. R-wave sensed event signals may also be passed to atrial event detector circuit 240 for use in setting time windows used by control circuit 206 in detecting atrial systolic events from the acceleration signal(s) received from sensor 212.

Atrial event detector circuit 240 is configured to detect atrial systolic events from a signal received from sensor 212. For example, an atrial event detection window may be set by atrial event detector circuit during which an atrial event detection threshold is applied to an acceleration vector signal or combination of acceleration vector signals received from selected accelerometer axes for atrial event sensing. An atrial event, also referred to herein as an "atrial systolic event" corresponding to atrial contraction or atrial systole, may be sensed when the threshold is crossed. Example techniques for detecting atrial events from an accelerometer signal are generally disclosed in U.S. Pat. No. 10,286,214 (Demmer, et al.), incorporated herein by reference in its entirety.

Atrial event detector circuit 240 passes an atrial event detection signal to processor 244 and/or pace timing circuit 242 in response to detecting an atrial event. Pace timing circuit 242 (or processor 244) may additionally receive R-wave sensed event signals from cardiac event detector 224 for use in controlling the timing of pacing pulses delivered by therapy delivery circuit 202. Processor 244 may include one or more clocks for generating clock signals that are used by pace timing circuit 242 to time out an AV pacing interval that is started upon receipt of an atrial event detection signal from atrial event detector circuit 240. Pace timing circuit 242 may include one or more pacing escape interval timers or counters that are used to time out various pacing escape intervals, which may be programmable intervals stored in memory 210 and retrieved by processor 244 for use in setting the pacing escape intervals, such as an AV pacing interval and a ventricular lower rate pacing interval.

Pace timing circuit 242 may start the lower pacing rate interval timer for controlling a minimum ventricular pacing rate. For example, if an atrial systolic event is not detected from the acceleration signals(s) received from sensor 212 triggering a ventricular pacing pulse at the programmed AV pacing interval, a ventricular pacing pulse may be delivered by therapy delivery circuit 202 upon expiration of the lower pacing rate interval (started upon a previous sensed or paced ventricular event) to prevent ventricular asystole and maintain a minimum ventricular rate. At times, control circuit 206 may control therapy delivery circuit 202 in a non-atrial tracking ventricular pacing mode (sometimes referred to as "asynchronous ventricular pacing"). The non-atrial tracking ventricular pacing mode may be denoted as a VVI pacing mode in which ventricular pacing pulses are delivered in the absence of a sensed R-wave and inhibited in response to an R-wave sensed event signal from sensing circuit 204. In some examples, dual chamber sensing may be performed during a non-atrial tracking ventricular pacing mode, e.g., a VDI pacing mode. A VDI pacing mode may include atrial event sensing from one, two or all three accelerometer axis signals for use in sensing atrial systolic events for detecting the heart rhythm.

In some cases, processor 244 receives an acceleration signal from one or more accelerometer axes for determining a patient physical activity metric and determining a sensor indicated pacing rate (SIR) for controlling the ventricular pacing rate based on patient activity level during a non-atrial tracking ventricular pacing mode, e.g., a VVIR pacing mode. One or more accelerometer axis signals may be used in determining the patient physical activity metric. Each accelerometer axis may be powered on and off at different times depending on the particular pacing therapy mode in effect. For example, during a VDD pacing mode, one, two or all three axes of a three dimensional accelerometer may be used to generate motion signals analyzed by processor 244 and/or atrial event detector circuit 240 for detecting atrial systolic events. At other times, one of the three axes of the accelerometer included in sensor 212 may be used for determining a SIR for controlling ventricular pacing, e.g., in the VVIR pacing mode. During the non-atrial tracking VVIR pacing mode, one or more accelerometer axis signals selected for producing an acceleration vector signal for atrial systolic event sensing may remain powered off.

Accordingly, the current drain required for powering operation of sensor 212 for producing an acceleration signal may vary dynamically over time. Additionally, the power required by control circuit 206 for processing and detecting atrial systolic events may vary dynamically over time as the pacing therapy delivery mode switches between an atrial tracking ventricular pacing mode and a non-atrial tracking ventricular pacing mode. Control circuit 206 may be configured to track the time that each axis of the accelerometer included in sensor 212 is "on" or powered by power source 214 for producing a motion signal from the respective axis. The cumulative "on" time for each accelerometer axis since the time of implantation of IMD 14 may be stored in memory 210 for use in determining a sensor operation current drain and estimating the longevity of power source 214 as described below.

Memory 210 may include buffers for storing the history of various functions and/or pacing modes over the operational history of IMD 14, e.g., from the time of implantation. Memory 210 may store a time stamp marking the time of implantation of IMD 14. From that time, memory 210 may store operational history of IMD 14. For example, memory 210 may include a sensor channel "on" time buffer 250 for storing the cumulative total time that each accelerometer axis is powered for generating an acceleration vector signal. Buffer 250 may include, for example, three memory locations for storing a total on time for each one of three accelerometer axes of sensor 212. Control circuit 206 may retrieve the total "on" time for each accelerometer axis for determining estimated power source longevity. In other examples, where sensor 212 includes more than one type of sensor, each type of sensor may correspond to a sensor "channel," and/or one or more sensors may each have multiple "channels" corresponding to different axes, directions, vectors or other sensing components of a given sensor. As such, in various examples, a sensor channel "on" time buffer 250 may store the total on time for each type of sensor and/or each sensor channel associated with a physiological sensor included in sensor 212.

Memory 210 may further include a therapy delivery mode time buffer 252 for accumulating the time that control circuit 206 operates in a specified therapy delivery mode. In particular, control circuit 206 may track the percentage of time that a therapy delivery mode is in effect that requires processing of signals from sensor 212 that may impose a relatively higher processing burden, and therefore current drain, than other therapy delivery modes. The processing burden required to analyze signals from sensor 212 for detecting cardiac events may require additional current drain from power source 214 that is not required during other therapy delivery modes. For example, control circuit 206 may at least track the time that IMD 14 is operating in a dual chamber sensing mode, e.g., VDD and/or VDI pacing mode. The processing burden for detecting atrial systolic events from the accelerometer signal increases the current drain from power source 214 compared to, for example, a single chamber sensing mode, e.g., a VVI or VVIR pacing mode, when ventricular event sensing (e.g., R-wave sensing) is performed by cardiac electrical signal sensing circuit 204, without requiring analysis of an accelerometer signal for detecting cardiac events. While operating in a rate responsive pacing mode, e.g., VVIR pacing mode, an accelerometer signal from sensor 212 may be used to determine a patient physical activity metric for adjusting the ventricular pacing rate. However, the processing burden to determine the physical activity metric, which may occur once every two seconds or less often, is relatively lower than the processing burden required to detect an atrial systolic event from the accelerometer signal as often as every cardiac cycle. As such, control circuit 206 may be configured to track and store accumulated time in one or more operating modes, e.g., therapy delivery modes, for use in estimating a power source longevity that takes into account the added processing burden required for detecting atrial systolic events from one or more acceleration vector signals received from sensor 212 to obtain a more reliable and accurate longevity estimate.

Accordingly, control circuit 206 may determine the cumulative time of operating in a dual chamber sensing mode since the time of IMD implantation and store the cumulative time in the dual chamber sensing mode in therapy mode time buffer 252. In particular, the cumulative time since implant that an operating mode, e.g., dual chamber sensing or atrial tracking ventricular pacing that requires atrial systolic sensing using accelerometer signals, may be stored in therapy mode time buffer 252. In one example, the cumulative time of operating in a VDD pacing mode is accumulated and stored.

Memory 210 may further store therapy delivery parameters that are used for estimating longevity of power source 214. For example, control circuit 206 may count all pacing pulses delivered by therapy delivery circuit 202 since the time of pacemaker implant. A total number of delivered pacing pulses may be stored in pacing parameter buffer 254, along with other pacing control parameters such as pacing pulse amplitude and pacing pulse width. The cumulative number of generated pacing pulses and currently programmed pacing pulse width and pacing pulse amplitude may be retrieved from memory 210 by control circuit 206 for use in estimating power source longevity.

In other examples, it is to be understood that the cumulative sensor operation time may be stored in memory of a medical device for one or more sensors and/or sensor channels associated with single chamber sensing, dual chamber sensing, or multi-chamber sensing. In a dual or multi-chamber pacemaker for example, memory 210 may additionally or alternatively store a history of the number of pacing pulses and/or other electrical stimulation pulses delivered to one or more heart chambers or therapy delivery sites. For example, the number of pacing pulses and/or other electrical stimulation pulses delivered to each of an atrial chamber and a ventricular chamber in a dual chamber pacing mode may be tracked for determining a therapy delivery current drain associated with dual chamber pacing. In still other examples, the number of pacing pulses and/or other electrical stimulation pulses delivered to each of an atrial chamber, the right ventricle and the left ventricle may be counted since the time of implant and stored for determining a therapy current drain associated with multi-chamber therapy, such as cardiac resynchronization therapy.

Memory 210 may accumulate the total time spent in one or more sensing and/or therapy delivery modes that may include single chamber, dual chamber and/or multi-chamber sensing and/or therapy delivery modes that each require processing of one or more sensor signals and therefore are each associated with a processing burden current drain. Accordingly, the techniques disclosed herein which are illustrated by the example of determining a sensor operation current drain, a processing burden current drain and a therapy delivery current drain of a single chamber ventricular pacemaker capable of dual chamber sensing for providing atrial tracking ventricular pacing may be expanded to determining sensor operation current drain, a processing burden current drain and/or a therapy delivery current drain of a dual chamber or multi-chamber pacemaker or ICD in other examples.

Therapy delivery circuit 202 may include charging circuit 230, switching circuit 232 and an output circuit 234. Charging circuit 230 may include a holding capacitor that may be charged to a pacing pulse amplitude by a multiple of the battery voltage signal of power source 214 under the control of a voltage regulator. The pacing pulse amplitude may be set based on a control signal from control circuit 206 based on a programmed pacing pulse amplitude stored in memory 210. Switching circuit 232 may control when the holding capacitor of charging circuit 230 is coupled to the output circuit 234 for delivering the pacing pulse. For example, switching circuit 232 may include a switch that is activated by a timing signal received from pace timing circuit 242 upon expiration of an AV pacing interval (or VV lower rate pacing interval) and kept closed for a programmed pacing pulse width (retrieved from memory 210) to enable discharging of the holding capacitor of charging circuit 230. The holding capacitor, previously charged to the pacing pulse voltage amplitude, is discharged across electrodes 162 and 164 through the output capacitor of output circuit 234 for the programmed pacing pulse duration.

In this way, therapy delivery circuit 202 generates pacing pulses delivered via electrodes 162 and 164 coupled to therapy delivery circuit 202 according to a therapy delivery mode of operation, e.g., VDD, VDI, VVI, VVIR, etc. Control circuit 206 may control switching between the various therapy delivery modes of operation, e.g., between a VDD pacing mode and a VVIR pacing mode to provide atrial synchronized ventricular pacing as much as possible but switch to a VVIR pacing mode when atrial tracking is undesirable, e.g., due to an atrial tachyarrhythmia or atrial systolic event undersensing or oversensing.

As indicated above, power source 214 provides power to sensor 212 to power on one or more selected accelerometer axes as needed for detecting cardiac events, e.g., atrial systolic events, and/or for determining patient physical activity and controlling a rate of therapy generated by therapy delivery circuit 202 according to the therapy delivery mode. Power source 214 further provides power to control circuit 206, e.g., to processing circuitry included in atrial event detector circuit 240 and processor 244 for detecting cardiac events from the acceleration vector signal(s) received from sensor 212. The pacing mode may change between an atrial synchronized ventricular pacing mode that requires sensing atrial events from the accelerometer signal and pacing modes that do not required sensing atrial events from the accelerometer signal. Depending on the characteristics of the acceleration vector signals, one, two or all three accelerometer axis signals may be selected for detecting the atrial events. Accordingly, current drain required from power source 214 for operating sensor 212 may vary over time, depending on the pacing mode and the number of accelerometer channels selected for use in detecting atrial events or sensing other motion such a patient physical activity. While longevity estimation may include determining a current drain to generate cardiac pacing pulses based on an average rate of pacing pulse delivery over time and the pacing pulse width and amplitude, the longevity estimation techniques disclosed herein take into account sensor operation current drain and processing burden current drain associated with operating sensor 212 and detecting cardiac events from the acceleration vector signal(s).

The techniques for estimating longevity as disclosed herein determine current drain required from power source 214 for functioning in an operating mode that requires operating sensor 212 and processing signals received by control circuit 206 from sensor 212. The current drain may include a sensor operation current drain based on the accumulated time, e.g., the percentage of time since implantation of IMD 14, that each accelerometer channel (e.g., each X, Y, and Z axis) has been powered on for producing an acceleration vector signal. The current drain may additionally or alternatively include a processing burden current drain based on the current from power source 214 required to power a processor included in control circuit 206 for processing the received acceleration vector signal(s) for detecting cardiac events, e.g., atrial systolic events, during an atrial tracking ventricular pacing mode or dual chamber sensing mode. As such the current drain used for estimating longevity may be determined based on the accumulated time, e.g., a percentage of time since implantation of IMD 14, that the IMD 14 has operated in a specified mode, e.g., an atrial-tracking ventricular pacing mode or any dual chamber sensing mode, that requires operation of sensor 212 and atrial event detection from the selected accelerometer channel signal(s). In other examples, the percentage of time of operating in one or more operating modes, which may be a sensing or therapy delivery mode, since implantation of a pacemaker or ICD may include single chamber, dual chamber and/or multi-chamber or multi-site sensing or therapy delivery modes.

Memory 210 may include computer-readable instructions that, when executed by control circuit 206, cause control circuit 206 to perform various functions attributed throughout this disclosure to IMD 14. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 210 may store timing intervals and other data used by control circuit 206 to control the delivery of pacing pulses by therapy delivery circuit 202, e.g., by detecting an atrial systolic event by atrial event detector circuit 240 from the accelerometer signal and setting a pacing escape interval timer included in pace timing circuit 242.

Memory 210 may further store instructions executed by control circuit 206 for estimating longevity of power source 214 between two voltage levels as described herein. Control circuit 206 may retrieve data from the various buffers 250, 252 and 254 as needed to execute the instructions. Control circuit 206 may execute the instructions on a scheduled basis, e.g., daily, weekly or monthly, or upon receipt of a command from an external device via telemetry circuit 208. Upon determining an estimated longevity, control circuit 206 may generate an output for storing in memory 210, e.g., corresponding to the estimated time to a recommended device replacement or end of service, which may be used in producing a notification transmitted by telemetry circuit 208.

Telemetry circuit 208 includes a transceiver 209 and antenna 211 for transferring and receiving data via a radio frequency (RF) communication link. Telemetry circuit 208 may be capable of bi-directional communication with external device 20 (FIG. 1) as described above. Sensor signals and cardiac electrical signals, and/or data derived therefrom may be transmitted by telemetry circuit 208 to external device 20. Programmable control parameters and algorithms for performing atrial event detection and ventricular pacing control may be received by telemetry circuit 208 and stored in memory 210 for access by control circuit 206. As described below, control circuit 206 may generate various notifications relating to estimated longevity of power source 214 and control telemetry circuit 208 to transmit notifications relating to the estimated longevity, such as recommended replacement time of the IMD 14 or end of service of power source 214.

In some examples, control circuit 206 may control telemetry circuit 208 to transmit data used by another medical device, e.g., external device 20 shown in FIG. 1, for performing longevity estimations. For instance, control circuit 206 may retrieve data from the buffers 250, 252, and 254 storing data correlated to current drain from power source 214 and pass the data to telemetry circuit 208 for transmission to another medical device. A processor included in another medical device may determine a power source longevity estimate using the transmitted data. In still other examples, control circuit 206 may determine a total current drain using data retrieved from memory 210, e.g., as described below in conjunction with FIG. 5, and transmit the total current drain or determined current drain components to another medical device via telemetry circuit 208 for performing longevity estimation. As such, the operations performed for estimating longevity between two voltages (associated with a known capacity change) of power source 214 may be performed cooperatively by one or more processors across one or more medical devices. As used herein, a "processor" configured to determine an estimated longevity according to the techniques disclosed herein may refer to multiple processors or processing circuitry distributed across one or more medical devices or computers in a medical device system, e.g., IMD processor 244 and external device processor 52 shown in FIG. 1.

The functions attributed to IMD 14 herein may be embodied as one or more processors, controllers, hardware, firmware, software, or any combination thereof. Depiction of different features as specific circuitry is intended to highlight different functional aspects and does not necessarily imply that such functions must be realized by separate hardware, firmware or software components or by any particular circuit architecture. Rather, functionality associated with one or more circuits described herein may be performed by separate hardware, firmware or software components, or integrated within common hardware, firmware or software components. For example, atrial systolic event detection from the sensor signal and ventricular pacing control operations performed by IMD 14 may be implemented in control circuit 206 executing instructions stored in memory 210 and relying on input from sensing circuit 204 and sensor 212. Providing software, hardware, and/or firmware to accomplish the described functionality in the context of any modern pacemaker, given the disclosure herein, is within the abilities of one of skill in the art.

Figure 4:
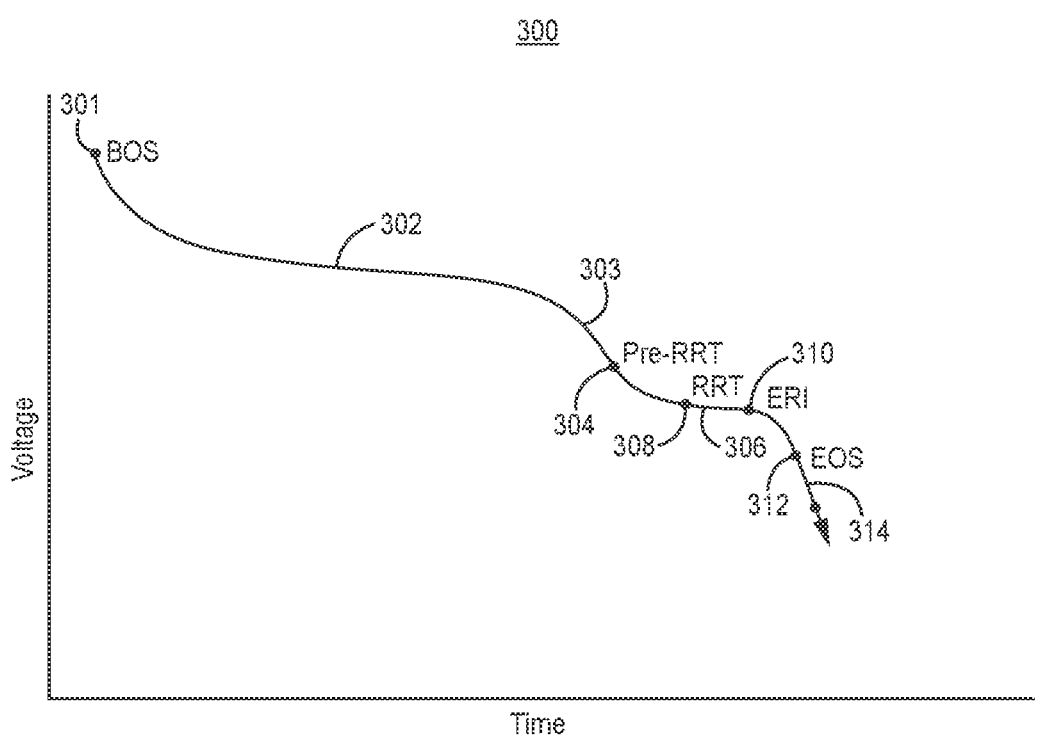
FIG. 4 is a graphical illustration of an IMD power source voltage over time since beginning of service.

FIG. 4 is a graphical illustration 300 of power source voltage over time. The voltage discharge curve shown in FIG. 4 represents the voltage depletion behavior of IMD power source 214 according to one example. Power source 214 has a starting voltage referred to as "beginning of service" (BOS) voltage 301, which may be power source voltage at the time of battery connection at the time of manufacture of IMD 14. The voltage may decrease from the BOS voltage 301 and remain relatively stable for an extended period of time as illustrated by the flat portion of voltage "plateau" 302. This first plateau portion 302 is followed by a first, relatively steep discharge portion 303 and a second, relatively shorter voltage plateau portion 306.

After the relatively short duration second plateau portion 306, the power source voltage may steeply decline as the power source depletes. An end of service (EOS) voltage 312 is reached during the second steep discharge portion 314. When the EOS voltage 312 is reached, the remaining capacity of power source 214 is insufficient to power the circuitry of IMD 14 for performing basic functions such as therapy delivery and sensing functions.

Since medical devices may be performing critical or lifesaving monitoring or therapy delivery, it may be desirable to determine when the power source 214 reaches a capacity that is greater than the EOS capacity, while still maximizing the useful life of the medical device. Accordingly, control circuit 206 may measure the power source voltage on a scheduled basis and determine when it has reached a reference voltage, e.g., a recommended replacement time (RRT) voltage 308. Control circuit 206 may be configured to generate a recommended replacement notification in response to detecting a specified reference voltage. Additionally or alternatively, when control circuit 206 measures the power source voltage and determines that it has reached a third, lower reference voltage 310, control circuit 206 may generate a notification indicating that the IMD power source 214 has reached an elective replacement time. This third reference voltage may be referred to as an elective replacement indicator (ERI) voltage 310 because it may be selected to shortly precede the second, steep discharge portion 314 that may quickly lead to EOS of the medical device. Accordingly, one or more reference voltages may be specified before the EOS voltage 312, e.g., along the second plateau portion 306 such as the RRT voltage 308 that occurs relatively early along the second plateau and the ERI voltage 310 that occurs relatively later along the second plateau 306, just prior to the final rapidly decreasing steep discharge portion 314 of the voltage discharge curve. When control circuit 206 measures the power supply voltage at or less than a reference voltage, control circuit 206 may generate a notification to be transmitted to an external medical device 20, to notify the patient or a clinician.

It may be desirable, however, to predict the time remaining between two voltage levels of power source 214 for generating notifications relating to the expected remaining usable life of the medical device in time to enable scheduling of medical device or power supply replacement procedures or power source recharging before the EOS voltage 312 is reached. The voltage level and time duration of the first plateau portion 302 may vary between devices, even of the same model, and due to different programmable control parameters and operating modes of the device. The voltage level may even fluctuate up and down slightly over the first plateau portion 302. Accordingly, if the voltage of power source 214 that is measured by control circuit 206 falls anywhere along the first plateau 302, it is difficult to predict where in time the measured voltage level is relative to a second lower voltage level since the voltage changes are relatively small along first plateau portion 302 and may fluctuate. An estimated power source longevity from a measured voltage along first plateau 302 until a second, lower voltage level may be an unreliable longevity estimate because it is difficult to estimate where in time the measured voltage is at along the relatively long duration first plateau 302.

A reference power source voltage 304 measured between the first plateau 302 and the second plateau 306, along the steep discharge portion 303 may be referred to as the pre-recommended replacement time (pre-RRT) voltage 304. This reference voltage, or pre-RRT voltage 304, may correspond to a reliably known remaining power source capacity. For example, through bench testing the remaining capacity of the power source 214 may be established at the reference pre-RRT voltage 304. In one example, the BOS voltage 301 is 3.2 Volts and corresponds to 100% remaining capacity, which may about 100 milliampere-hours as an example. The pre-RRT voltage 304 may be 2.65 Volts, corresponding to 25% remaining capacity or about 25 milliampere-hours in one illustrative example. It is to be understood, however, that the BOS voltage 301 and any reference voltages selected from a power supply discharge curve for use in estimating longevity between two reference voltages are not limited to any particular BOS power source voltage and capacity or any particular discharge voltage curve characteristics. BOS voltage of batteries used in IMDs may range from 1 to 10 Volts and capacities up to 1 to 2 ampere-hours or higher, as examples, with no limitation intended. The power source may discharge with no plateau, a single plateau, two plateaus as shown in the example of FIG. 4, or more than two plateaus.

In one example, power source 214 includes one or more hybrid primary cells including lithium, carbon fluoride and silver vanadium oxide. Other battery chemistries used in a medical device that implements the longevity estimation techniques disclosed herein may include lithium based cells such as, but not limited to, lithium iodide, lithium iodine, lithium manganese dioxide, lithium silver vanadium oxide, lithium poly-carbon monofluoride, lithium-silver chromate, lithium copper sulfide, lithium thionyl chloride or hybrids thereof as well as non-lithium based cells such as battery chemistries including zinc or nickel cadmium. The longevity estimation techniques disclosed herein may be implemented in conjunction with any desired battery chemistry and BOS capacity, as long as at least one specified voltage along the discharge curve can be reliably measured and is associated with a known remaining capacity. A second lower voltage may be the EOS voltage 312 having zero remaining capacity. In other examples, the second lower voltage may be greater than the EOS voltage and associated with a known remaining capacity such that the capacity difference between the first reference voltage and the second lower reference voltage is known.

In the example of FIG. 4, the remaining battery capacity can be reliably known for a reference voltage that occurs along the relatively steep discharge portion 303. Using this reference voltage associated with a known remaining battery capacity, the estimated longevity of power source 214 until a second, lower voltage associated with a second remaining capacity, e.g., the EOS voltage 312, may be determined. The estimated longevity may be determined as the number of days (or other units of time) from the pre-RRT voltage to the EOS voltage in some examples, but it is to be understood that the techniques disclosed herein may be used to estimate longevity between any two selected voltages, each associated with an established remaining power source capacity.

As described below, control circuit 206 may measure the power source voltage at scheduled time intervals or scheduled times of day. When the pre-RRT voltage 304 is reached, this is an indication that the power source voltage is transitioning from the first plateau 302 to the second plateau 306. When the reference pre-RRT voltage 304 associated with a known remaining power source capacity is reached, control circuit 206 is triggered to perform a longevity estimate. The longevity may be estimated based on determining a total current drain using historical data stored in memory 210 and the known remaining capacity at the pre-RRT voltage 304 and the known remaining capacity at the second lower voltage, which may be 0 at the EOS voltage 312.

Control circuit 206 may include a timer or counter to begin counting the number of days (or other longevity time unit) elapsed since the pre-RRT voltage 304 was measured. The longevity estimate may be repeated at scheduled time intervals or scheduled times of day until the EOS voltage 312 is reached (or until IMD 14 or power source 214 is replaced or recharged). The estimated longevity may be determined daily, for example, based on the pre-RRT voltage capacity and based on the updated values stored in the sensor channel "on" time buffer 250, therapy delivery mode time buffer 252 and pacing parameter buffer 254. However, after the pre-RRT voltage is reached, control circuit 206 may count the number of days already elapsed since the pre-RRT voltage is reached and subtract that number of elapsed days from the longevity estimated based on the pre-RRT voltage capacity. When the estimated longevity reaches a threshold number of days specified as a RRT or ERI, control circuit 206 may generate a notification via telemetry circuit 208 to make the patient and/or a clinician aware that IMD 14 or power source replacement or recharging is recommended or required to avoid reaching the EOS voltage 312.

Figure 5:
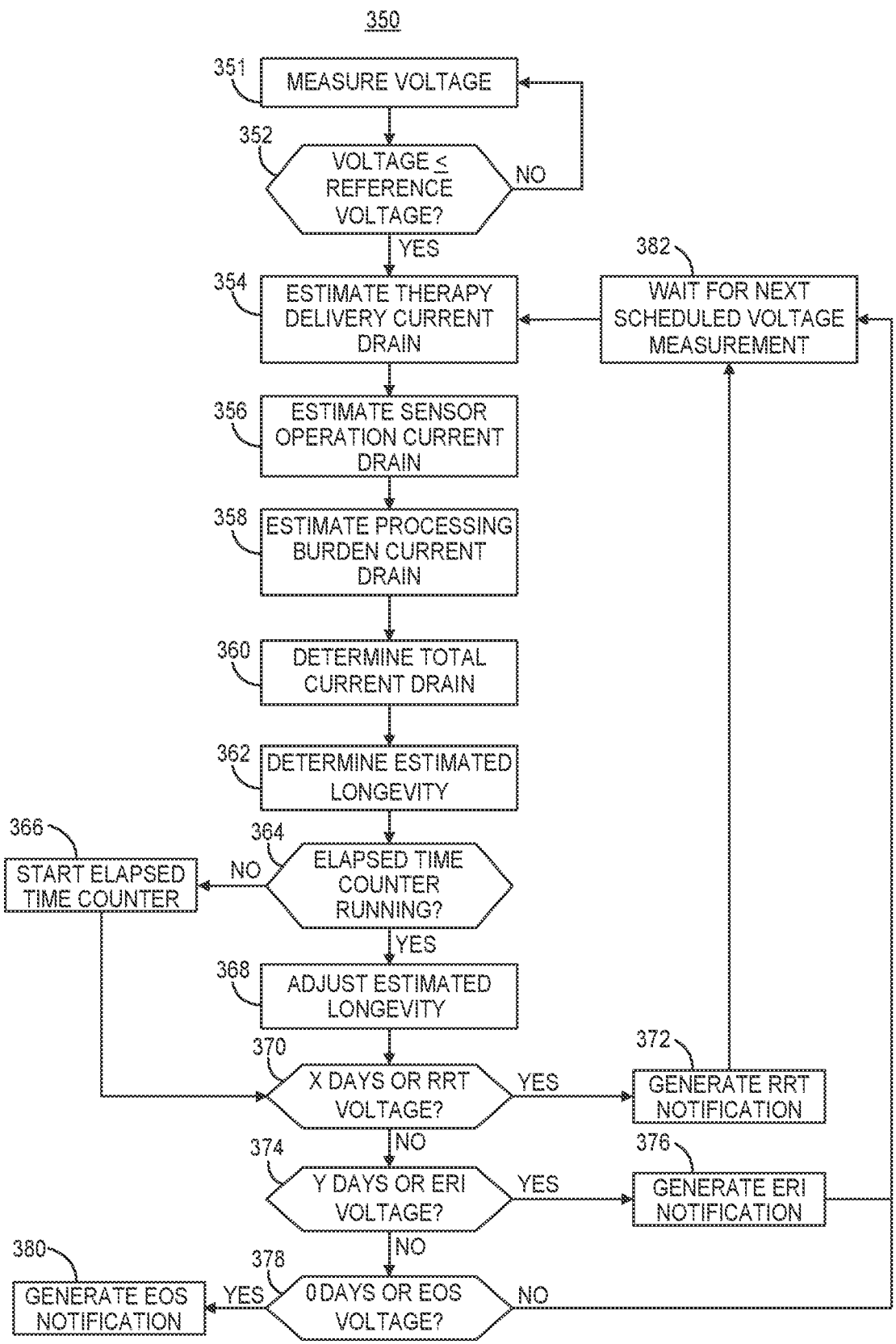
FIG. 5 is a flow chart of a method for determining a predicted time between two voltage levels of the IMD power source according to one example.

FIG. 5 is a flow chart 350 of a method for determining an estimated time between two voltage levels of a medical device power source according to one example. The techniques disclosed herein may be applied to a power source including one or more non-rechargeable primary batteries and/or rechargeable batteries. The process of flow chart 350 may be performed periodically, e.g., daily or other scheduled basis, to estimate the longevity of the power source of the medical device, e.g., power source 214 of IMD 14. The process shown by flow chart 350 and other flow charts presented herein may be performed by a processor included in the same device as the power source for which longevity is being estimated. In other examples, the process for estimating longevity may be performed all or in part by a processor of another medical device or computer after receiving data required for determining the longevity from the medical device, e.g., external device processor 52. For the sake of convenience, the process for estimating the longevity as the estimated time from a first voltage to a second voltage of a power source is described as being performed by control circuit 206, e.g., by processor 244, but it is to be understood that external device processor 52 may perform operations for determining the estimated time in some examples. For example, processor 52 may receive data transmitted from IMD 14 for determining the estimated time. The function of determining the estimated time may therefore be distributed across two or more processors in some examples.

At block 351, control circuit 206 measures the voltage of the power source 214. For example, battery voltage of power source 214 may be measured daily or according to another predetermined schedule. In some examples, the battery voltage may be measured at a single time point for each scheduled measurement. In other examples, a scheduled measurement may include measuring the battery voltage at multiple time points and averaging the multiple measurements.

In some examples, control circuit 206 may estimate longevity of power source 214 only when the measured power source voltage is equal to or less than a specified reference voltage. Accordingly, control circuit 206 may compare the measured voltage to a reference voltage at block 352. When the measured voltage is greater than the reference voltage, control circuit 206 may return to block 351 to wait for the next scheduled voltage measurement. When the measured voltage is greater than the reference voltage, the expected medical device longevity may be relatively long, e.g., greater than 6 months or more for an IMD or greater than 24 hours or more for a rechargeable device, such that any notifications regarding the remaining service life of the medical device may be deemed unnecessary or non-urgent. In some cases, the longevity may be difficult to estimate when the measured voltage is greater than the reference voltage depending on the discharge properties of the power source. For example, when the measured voltage is along the first plateau portion 302 of the discharge curve of FIG. 4, a longevity estimate may be unreliable. As such, the reference voltage at block 352 may be the pre-RRT voltage 304 as shown in FIG. 4, which may be a voltage along the first steep discharge portion 303 following the first plateau portion 302. The pre-RRT voltage 304 may be specified based on bench testing performed to characterize the discharge curve of the power source. In one example, the pre-RRT voltage is 2.65 volts for a power source having a beginning of service voltage of about 3.2 volts.

The specified reference voltage may be any voltage that can be reliably measured and is associated with a known remaining power source capacity. For example, the remaining battery capacity when the pre-RRT voltage 304 is reached may be reliably known to be about 25% of the starting or BOS battery capacity. The longevity of the power source 214 can be estimated using the known remaining battery capacity at the reference voltage level, e.g., at the pre-RRT voltage, and estimating the total current drain required for sensing and therapy delivery operations based on historical data acquired by control circuit 206 and programmed therapy control parameters.

To estimate the current drain required to continue operating according to expected patient need, control circuit 206 may estimate a therapy delivery current drain at block 354, a sensor operation current drain at block 356 and a processing burden current drain at block 358 based on the history of the medical device operation, e.g., since the BOS or time of implantation of IMD 14. At block 354, the therapy delivery current drain may be estimated based on therapy delivery history and currently programmed therapy control parameters. Example methods for estimating the therapy delivery current drain are described below in conjunction with FIG. 6.

At block 356, control circuit 206 may estimate a sensor operation current drain. The sensor operation current drain may be determined based on a history of the sensor operation and/or programmed sensor operation control parameters. In illustrative examples presented herein, the sensor operation current drain is estimated for operating a three-axis accelerometer. In other examples, however, other types of physiological sensors may be included in the medical device that is performing the longevity estimate according to the techniques disclosed herein. Other types of sensors may include a pressure sensor, an optical sensor such as a tissue or blood oxygen sensor, an acoustical sensor, an ultrasonic sensor, a flow sensor or the like. In some examples, multiple sensors and/or multiple sensor channels of a given sensor may be included in the medical device. For instance, multiple sensor channels may be provided where each channel corresponds to a different vector, axis or direction, a different frequency or other component of operation, and/or different signal processing or analysis (e.g., different signal filtering, signal amplification, sampling rate, determination of signal features, etc.). Accordingly, the sensor operation current drain estimated at block 356 may be based on a history of the total time that each sensor and/or sensor channel included in sensor 212 of FIG. 3 is powered on for producing a signal from which control circuit 206 may detect a physiological event or determine a physiological parameter.

A processing burden current drain may be estimated at block 358 by control circuit 206. The processing burden current drain may be associated with one or more operating modes of the medical device which require different degrees of signal processing and analysis compared to other operating modes of the medical device. The processing burden may depend on processing that is required to control therapy delivery. However, in some examples, the processing may be required for monitoring a physiological signal and producing an alert or notification of a medical condition. In examples presented herein, the processing burden current drain depends on the percentage of time that IMD 14 has historically operated in a sensing or therapy delivery mode, e.g., a specified cardiac pacing mode, which requires processing and analysis of one or more sensor signals. For example, when IMD 14 is operating in an atrial-tracking ventricular pacing mode, dual chamber sensing is required including detecting atrial systolic events from one or a combination of accelerometer axis signals. The processing burden current drain during the atrial-tracking ventricular pacing mode is relatively greater than the processing burden current drain during a non-atrial tracking ventricular pacing mode due to the processing required to sense (detect) atrial systolic events from the accelerometer axis signals during the atrial-tracking ventricular pacing mode. Example methods for determining processing burden current drain are described below in conjunction with FIG. 6.

At block 360, the total current drain is determined by summing the estimated therapy delivery current drain, the sensor operation current drain, and the processing burden current drain. The total current drain may further include an estimated static current drain to account for current from the power source required to power basic IMD functions that may have limited variability over time compared to changes in therapy delivery, sensor operation and processing burden associated with switchable sensing and/or therapy delivery modes. For example, a static current drain component of the total current drain determined at bock 360 may take into account current required to operate cardiac electrical signal sensing circuit 204 for sensing cardiac electrical events on a beat-by-beat basis and other ongoing functions of control circuit 206. This static current drain is expected to remain relatively constant over the functional life of IMD 14 and may therefore be included in the total current drain determined at block 360 as a fixed value, which may be stored in memory 210.

At block 362, the total current drain may be converted to an estimated time until a second, lower voltage level associated with a second remaining battery capacity. For example, the total current drain may be converted to an estimated longevity from the pre-RRT voltage along a steep slope of the discharge curve until an EOS voltage level, associated with 0% remaining capacity. The longevity may be determined at block 362 as a number of days remaining from a first measured battery voltage level, e.g., the reference pre-RRT voltage level having a known remaining capacity, until a second, lower battery voltage level, e.g., the EOS voltage. For example, the longevity in days from the pre-RRT voltage until the EOS voltage may be determined by converting the total current drain to longevity in days by dividing the capacity difference between the first and second voltages (e.g., in ampere-hours) at the pre-RRT voltage by the total current drain (in amperes) and dividing this result by 24 hours per day. Depending on the medical device, the estimated longevity may be determined in other units of time such as hours, weeks, months or years.

At block 364, control circuit 206 may determine whether an elapsed time counter is running. The elapsed time counter may be started at block 366 when the reference pre-RRT voltage is first reached to begin counting the number of days (or other time units) that elapse after the power source voltage reaches the reference pre-RRT voltage. For example, the number of days may be counted up beginning from the time that the measured power source voltage is at the pre-RRT voltage. The power source voltage measurements may have a resolution of less than 10 millivolts, e.g., about 7 millivolts. As such, the determination of when the power source voltage reaches the reference pre-RRT voltage may be within a margin of error of two days or less or even one day or less.

When the elapsed time counter is already running at block 364 (e.g., started previously in response to the first estimated longevity determined upon reaching the reference pre-RRT voltage), control circuit 206 may adjust the estimated longevity determined at block 362 (and stored in memory 210) based on the capacity at the reference pre-RRT voltage by subtracting the number of days counted by the elapsed time counter since the pre-RRT voltage was reached. In this way, a new estimated longevity determined one or more days after the pre-RRT voltage has been reached, using the known power source capacity at the reference pre-RRT voltage, may be adjusted by the actual number of days already elapsed. This adjusted estimated longevity determined at block 368 corresponds to the longevity remaining from the current power source voltage that is less than the reference pre-RRT voltage.

In an illustrative example, when the measured battery voltage is at the pre-RRT, the estimated longevity determined the first time by control circuit 206 at block 362 may be 500 days. The elapsed time counter is at 0 and begins counting the number of days that elapse since the pre-RRT voltage was measured. The longevity estimated at block 362 at a later time point based on the pre-RRT voltage capacity and new estimates of therapy delivery current drain, sensor operation current drain and processing burden current drain may be 350 days. The pre-RRT voltage capacity is used to determine the estimated longevity because the power source capacity at the pre-RRT voltage is known whereas the remaining power source capacity at the currently measured power source voltage, less than the pre-RRT voltage, may be unknown. The elapsed time counter may have reached a value of 50 days since the pre-RRT voltage was reached. The adjusted estimated longevity at block 368 is therefore 350 days minus 50 days that have already elapsed since the pre-RRT voltage was reached giving an adjusted longevity of 300 days until the EOS voltage in this example. The adjusted longevity may not alter the value of the elapsed time counter. The elapsed time counter tracks the number of days since the pre-RRT voltage was reached so that future longevity estimates determined based on the remaining battery capacity at the pre-RRT voltage can be adjusted by the number of days that have already actually elapsed since the pre-RRT voltage was measured.

If the estimated longevity, which may be the adjusted estimated longevity based on the elapsed time counter, reaches a first threshold number of days remaining (block 370), a recommended replacement time (RRT) notification may be generated at block 372. In one example, when the estimated longevity is 180 days, an RRT notification is generated. The RRT notification may be transmitted via telemetry circuit 208 to an external device, e.g., external device 20, the next time an interrogation command is received from the external device 20.

When the adjusted estimated longevity reaches a second, lower threshold number of days (block 374), control circuit 206 may generate an elective replacement indicator (ERI) notification at block 376. The second lower threshold number of days may be 30 to 90 days, as examples. The ERI notification may indicate to a clinician that the IMD 14 or power source 214 should be replaced or recharged in order to avoid reaching the EOS voltage and a disruption in therapy delivery. The control circuit 206 may continue to measure the power source voltage at block 382 and determine longevity estimates until the longevity estimate reaches zero days remaining at block 378. When the estimated longevity is zero days, an end of service (EOS) notification may be generated at block 380 by control circuit 206 and transmitted to an external device by telemetry circuit 208.

The power source voltage measurement performed on a scheduled basis, e.g., each day at the same time that the longevity is determined, may also trigger an RRT, ERI or EOS notification in some examples. For instance if the RRT voltage, ERI voltage or EOS voltage (as shown in the discharge curve of FIG. 4) is reached (as determined at blocks 370, 374 or 378, respectively) before the adjusted longevity estimate reaches the threshold number of days, control circuit 206 may generate a notification (at block 372, 376 or 380) based on the measured battery voltage. The generated notification may be stored in memory 210 for transmission via telemetry circuit 208. In this way, the measured power source voltage may be a backup trigger for an RRT, ERI and/or EOS notification when the power source voltage reaches a corresponding threshold voltage before the adjusted estimated longevity reaches the threshold number of days for generating an RRT, ERI or EOS notification. Once the EOS number of days or EOS voltage is reached, the process of FIG. 5 may be terminated such that no further power source voltage measurements or longevity estimates are determined. Until the EOS notification is generated, however, power source voltage measurements and determination of the longevity estimate may continue as scheduled, e.g., daily.

Figure 6:
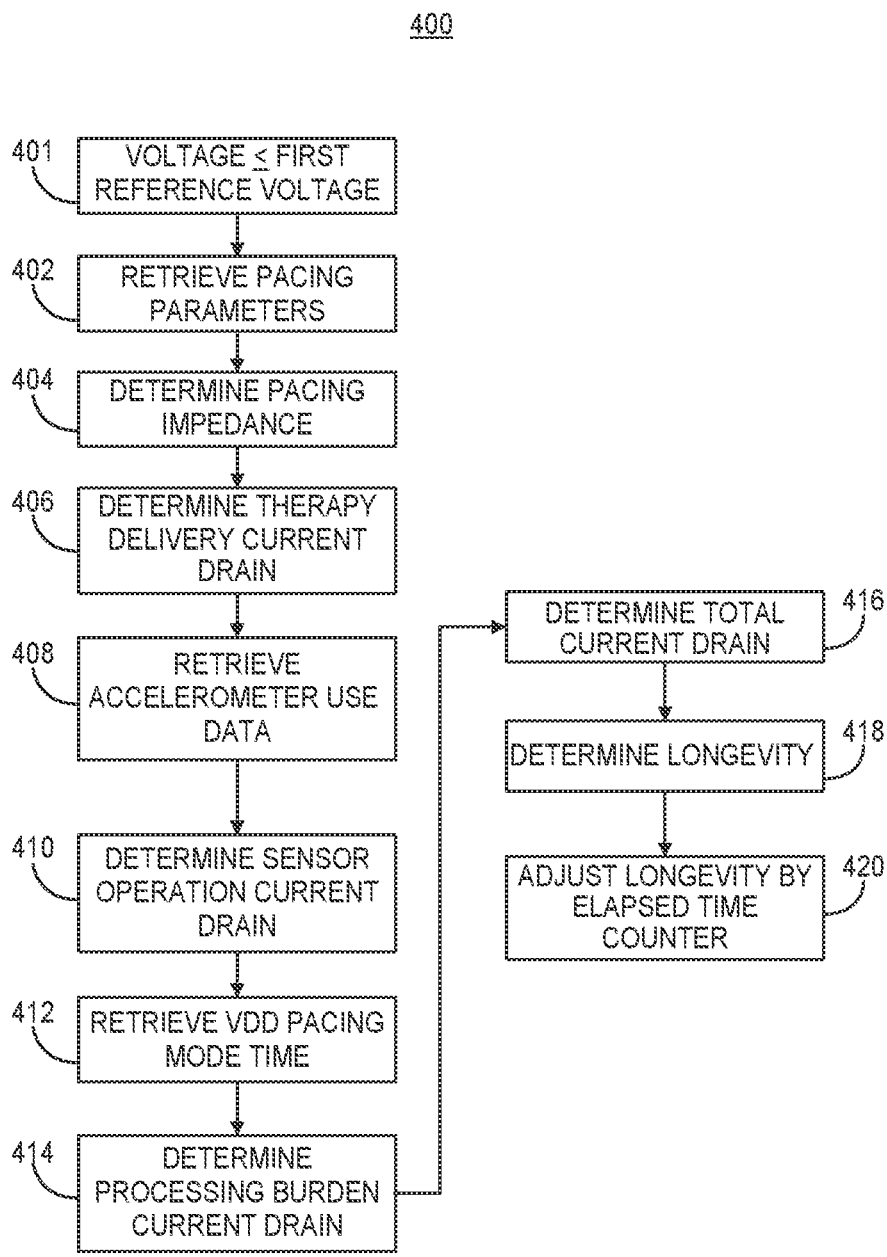
FIG. 6 is a flow chart of a method for determining a total current drain and estimated longevity of an IMD according to some examples.

FIG. 6 is a flow chart 400 of a method for determining the total current drain and estimated longevity according to some examples. The process of flow chart 400 may be performed when the measured power source voltage is less than or equal to a first reference voltage, e.g., the pre-RRT voltage or other specified reference voltage that corresponds to a known remaining power source capacity, as determined at block 401. At scheduled time intervals or a scheduled time of day, control circuit 206 may measure the battery voltage of power source 214. After the pre-RRT voltage is reached, the process of determining the estimated longevity is performed and may be repeated on a scheduled or triggered basis or upon receiving a command from another medical device.

In some examples, once the first reference voltage is reached and the elapsed time counter is started to count the number of days since the first reference voltage was reached, the power source voltage measurements are optional. The power source voltage is not required for determining the estimated longevity after the reference voltage is reached. As described above, the estimated longevity may be computed using the known remaining battery capacity at the pre-RRT voltage, the estimated total current drain, and the actual number of days elapsed since the pre-RRT voltage was measured. However, as described above, the power source voltage measurement may be performed each time longevity is estimated so that the actual battery voltage may trigger a replacement notification or EOS notification.

At block 402, control circuit 206 retrieves pacing control parameters for use in determining a therapy delivery current drain. In one example, the currently programmed pacing pulse width and pacing pulse amplitude are retrieved from memory 210. At block 404, control circuit 206 may determine the pacing impedance. For example, control circuit 206 may control therapy delivery circuit 202 to apply a drive signal (current or voltage) to the electrodes 162 and 164 to enable recording of the resulting signal (voltage or current) for use in determining a pacing impedance. In other examples, a previously measured pacing impedance stored in memory 210 may be retrieved for use in determining the pacing current drain.

At block 406, the therapy delivery current drain is determined using the retrieved pacing pulse amplitude and pacing pulse width settings and the measured pacing impedance. In some examples, the therapy delivery current drain is determined by retrieving a current drain value from a look up table (LUT) stored in memory 210 (or memory 53 of external device 20 when processor 52 is determining the estimated longevity).

Figure 7:
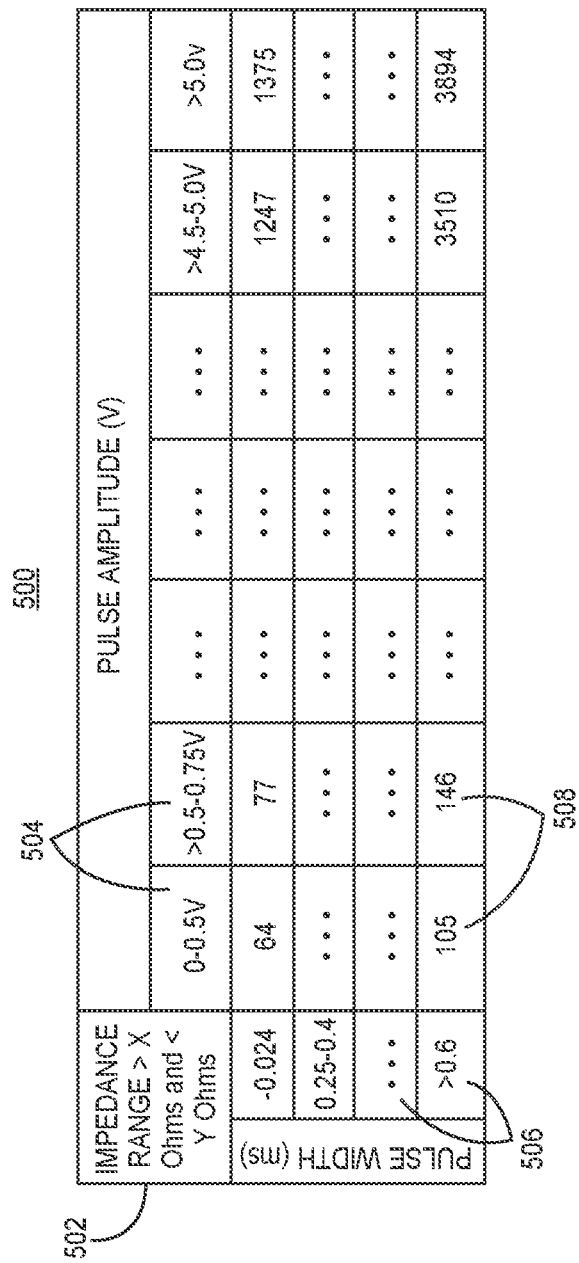
FIG. 7 is an example look-up table of therapy delivery current drain values stored in an IMD according to one example.

FIG. 7 is one example of a LUT 500 storing therapy delivery current drain values. Multiple LUTs may be stored in memory 210 with each LUT corresponding to a specified pacing parameter. Each LUT may store current drain values associated with multiple combinations of two other pacing parameter values for a specified range of a third pacing parameter value. In the example of FIG. 7, the LUT 500 corresponds to a specified pacing impedance range 502, e.g., greater than X ohms and less than or equal to Y ohms. Two, three or more LUTs may be stored in memory 210, each corresponding to a different pacing impedance range. For example, one LUT may be stored for pacing impedance up to and including 450 Ohms. A second LUT may be stored for pacing impedance greater than 450 Ohms and less than or equal to 550 Ohms. A third LUT may be stored for pacing impedance greater than 550 Ohms.

The LUT 500 includes pacing current drain values 508 stored for each combination of multiple pulse amplitude settings 504 and multiple pulse width settings 506. Control circuit 206 selects the pacing current drain value from LUT 500 corresponding to the retrieved pacing pulse width and pacing pulse amplitude. To illustrate, when pacing impedance falls in the range 502 specified for LUT 500, the pacing pulse amplitude is 0.6 volts (second column) and the pacing pulse width is 0.24 (first row), the pacing current drain value retrieved from LUT 500 is 77 (in 8 bit math). It is recognized that LUTs may be formatted according to different combinations of pacing parameters than the specific example of FIG. 7. For example, each LUT may be stored for a specified value or range of pacing pulse amplitude with multiple current drain values for each combination of different pacing impedance ranges and pacing pulse width ranges. In various examples, LUTs may store current drain values for combinations of two pacing parameters, three pacing parameters, four pacing parameters or more and numerous arrangements of the pacing parameters in the LUT(s) are possible. Other pacing parameters that may be accounted for in a LUT may include pacing rate, pacing frequency, or therapy delivery mode.

For example, when dual chamber or multi-chamber pacing therapies are being delivered, additional LUTs may be provided for each heart chamber or pacing site. For instance, one or more LUTs may store current drain values associated with delivering atrial pacing pulses and another set of one or more LUTs may store current drain values associated with delivering ventricular pacing pulses. In other instances, a single set of LUTs may be expanded to include appropriate pacing parameter ranges, e.g., pacing impedance, pacing pulse amplitude and/or pacing pulse width, that would pertain to all of the heart chambers or sites that pacing therapy is being delivered to. For example, a LUT may store current drain values for ranges of pacing pulse amplitude and pacing pulse width that span all available settings of both atrial pacing control parameters and ventricular pacing control parameters. These LUTs may be stored for multiple ranges of pacing impedance that span an expected range of both atrial and ventricular pacing impedance. In this way, an appropriate current drain value can be stored in a LUT (or set of LUTs) for retrieval for determining a therapy delivery current drain associated with therapy delivered to each heart chamber or multiple heart locations.

The pacing current drain values stored in LUT 500 may represent the pacing current drain expected for the corresponding pulse amplitude, pulse width and pacing impedance when therapy delivery circuit 202 is generating pacing pulses at a specified rate. In one example, the current drain values stored in each LUT correspond to pacing 100% of the time at a rate of 60 pulses per minute. Accordingly, control circuit 206 may adjust the pacing current drain value retrieved from a LUT based on the actual pacing frequency since implantation. Control circuit 206 may be configured to count the total number of pacing pulses generated by therapy delivery circuit 202 since IMD implantation. Control circuit 206 may be further configured to track the total time since implant or since the last longevity estimate. These values of total number of generated pacing pulses and total time since implant may be tracked by a counter included in control circuit 206. The pacing current drain retrieved from the LUT 500 may be multiplied by the total number of pacing pulses since implant divided by the time since implant to adjust the retrieved current drain according to the actual pacing frequency since implant.

Thus, at block 406 of FIG. 6, control circuit 206 determines the therapy delivery current drain by retrieving the pacing current drain from a LUT stored in memory 210 for the determined pacing pulse width, amplitude and impedance and corresponding to an assumed pacing frequency. The retrieved pacing current drain is adjusted to correspond to the actual pacing frequency using a stored total number of generated pacing pulses and a stored total time since implant. This adjusted pacing current drain is determined as the therapy delivery current drain at block 406.

When the medical device delivers therapy to multiple heart chambers, heart locations, or more generally multiple therapy delivery sites, a therapy delivery current drain may be determined for each therapy delivery site and summed to determine the therapy delivery current drain. The therapy delivery current drain determined for each site may be determined by retrieving a current drain from a LUT for the pacing parameters specific to that therapy delivery site and adjusting the LUT current drain by the percentage of time since implant that therapy has been delivered to that therapy delivery site. For example, in a dual chamber or multi-chamber pacemaker, an atrial therapy current drain and a ventricular therapy current drain (for each of one or both ventricles) may be determined and summed to determine a total therapy delivery current drain.

In other examples, multiple LUTs may each store current drain values associated with different therapy delivery modes. For example, at least one LUT may store current drain values for single chamber therapy; at least one LUT may store current drain values for dual chamber therapy and/or at least one LUT for multi-chamber therapy. In this case, a current drain value for each therapy delivery mode, e.g., single chamber and dual chamber pacing modes for example, can be retrieved from a respective single chamber pacing mode LUT and dual chamber pacing mode LUT. The retrieved current drain values may be adjusted for the percentage of time spent in the respective single chamber pacing mode and dual chamber pacing mode to determine respective single chamber pacing therapy current drain and dual chamber pacing therapy current drain. The pacing mode current drains may be summed to determine a total therapy delivery current drain.

At block 408 of FIG. 6, control circuit 206 retrieves the total "on" time for each accelerometer axis of sensor 212 over the operational life of the IMD 14, e.g., since the implantation of the IMD 14. The total "on" time for each accelerometer axis may be accumulated and stored in memory 210 by control circuit 206, e.g., in buffer 250, as described above. Since the accelerometer axes may be selected one at a time, two at a time, or three at a time for generating acceleration vector signals, each channel may have a different total "on" time. Furthermore, one or more accelerometer axes may be selected for monitoring patient activity during a rate responsive pacing mode. For example, when IMD 14 is configured to switch between an atrial tracking VDD pacing mode and a non-tracking, rate responsive VVIR pacing mode, the total "on" time per accelerometer axis will depend on which axes are selected for generating acceleration signals for sensing atrial systolic events and for tracking patient physical activity and the relative amounts of time spent in each therapy delivery mode.

The power source current drain for each accelerometer axis is determined by multiplying the retrieved total "on" time for a given axis by a predetermined accelerometer current drain per channel. The three current drains determined for each of the three axes of the accelerometer may be summed to determine the sensor operation current drain at block 410.

At block 412, control circuit 206 may retrieve the total time spent in a VDD pacing mode since the time of implant. As described above, control circuit 206 may be configured to switch between two or more pacing modes for controlling therapy delivery circuit 202 in generating pacing pulses. An atrial-tracking ventricular pacing mode may include sensing an atrial systolic event from one or more acceleration vector signals received from sensor 212, which may include powering one or more selected accelerometer axes. The sensor operation current drain determination accounts for the current drain required to operate the accelerometer axes selected for producing an acceleration signal from which the atrial systolic events can be detected. However, control circuit 206 performs signal analysis on the received accelerometer axis signal(s) in order to detect the atrial systolic event on a beat-by-by beat basis to enable a ventricular pacing pulse to be generated at an atrioventricular interval following each atrial systolic event detection. This atrial-tracking ventricular pacing mode, e.g., VDD pacing mode, therefore requires greater processing power and current drain than a non-atrial tracking ventricular pacing mode, e.g., a VVI pacing mode or a VOO pacing mode that does not require detecting atrial systolic events from the acceleration signal on a beat-by-beat basis.

As such, in order to improve the accuracy of the estimated longevity, the total time since implant spent in the VDD pacing mode may be tracked by control circuit 206. The percentage of time spent in the VDD pacing mode may be multiplied by a predetermined processing current drain required for detecting atrial systolic events by control circuit 206. This processing burden current drain determined at block 414, and the sensor operation current drain determined at block 410, both represent a current drain from power source 214 that is required to operate in a particular therapy delivery mode, e.g., an atrial tracking ventricular pacing mode, that requires generation and analysis of a physiological signal by sensor 212 in order to control the therapy delivery. The physiological signal generated by sensor 212, e.g., the acceleration vector signal(s), is different than the cardiac electrical signal sensed by cardiac electrical signal sensing circuit 204. The generation of this additional physiological signal and processing and analysis thereof as required for a particular therapy delivery mode increases the current drain from power source 214 and is therefore taken into account in the estimated longevity techniques disclosed herein. In various examples, at least the sensor operation current drain and/or the processing burden current drain corresponding to an operating mode that requires processing and analysis of the sensor signal is determined for estimating power source longevity.

In the example of FIG. 6, the processing burden current drain is determined based on a percentage of time since implant that control circuit 206 is operating in a particular therapy delivery mode. In other examples, the processing burden current drain may be determined based on the percentage of time that the medical device is operating in one or more sensing and/or therapy delivery operating modes. For instance, control circuit 206 may track the total time of operating in a dual chamber sensing mode that requires processing and analysis of the accelerometer signal for detecting atrial systolic events. In other examples, the processing burden current drain may be determined for two or more operating modes of the medical device. A portion of the processing burden current drain may be determined for each one of multiple operating modes, where each operating mode is associated with a different processing current requirement that is multiplied by the percentage of time the medical device operates in the associated operating mode. The processing burden for each of the multiple operating modes may be summed to obtain the total processing burden current drain.

At block 416 the total current drain is determined by summing the therapy delivery current drain, the sensor operation current drain, the processing burden current drain and any predetermined static current drain for powering basic IMD functions that require relatively constant current drain over the functional life of the IMD. At block 418 the longevity based on the difference between the power source capacity associated with the first reference voltage and the power source capacity associated with a second, lower reference voltage is determined. The estimated longevity between the two voltage levels is obtained by dividing the capacity difference by the total current drain then converting to the desired unit of time. For example, the capacity difference in ampere-hours divided by current drain in amperes may be divided by 24 hours/day to obtain an estimated longevity from the first voltage to the second voltage in days. In some examples, the first voltage is the pre-RRT voltage shown in FIG. 4 and the second voltage is the EOS voltage and the capacity difference between the pre-RRT voltage and the EOS voltage may be established to be 25% of the BOS capacity.

At block 420, the estimated longevity from the first voltage to the second voltage may be adjusted by subtracting the actual number of days already elapsed since the first reference voltage was measured. This adjusted estimated longevity may be compared to the longevity thresholds for determining when an output, such as a notification recommending replacement or an EOS notification, should be generated (as described above in conjunction with FIG. 5).

Figure 8:
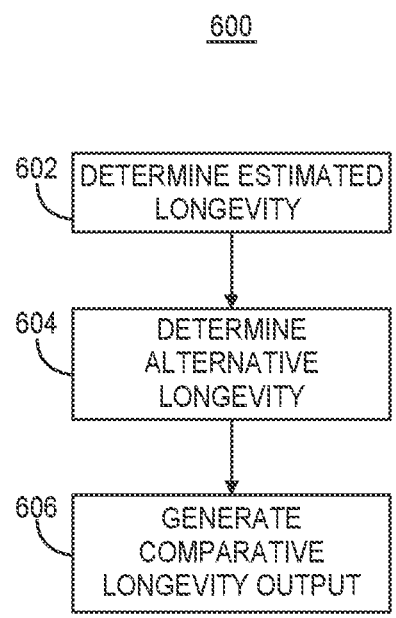
FIG. 8 is a flow chart of a method that may be performed by a medical device system for determining comparative longevity estimates according to one example.

FIG. 8 is a flow chart 600 of a method that may be performed by a medical device system, e.g., IMD system 10 of FIG. 1, for determining comparative longevity estimates according to one example. At block 602, the longevity may be estimated by determining the estimated time between two power source voltages, each associated with a specified remaining power source capacity, using historical data and currently programmed control parameters. The longevity estimated at block 602 may be determined according to the example techniques described above in conjunction with FIGS. 5 and 6. For instance, data accumulated and stored by the medical device relating to the accumulated "on" time of each channel or axis of a physiological sensor and/or stored data relating to the total time spent operating in one or more operating modes corresponding to different processing current drain requirements may be retrieved for determining the estimated longevity based on historical operation of the medical device.

At block 604, a processor of the medical device system may determine one or more alternative longevities. For example, the processor 52 of external medical device 20 may determine an alternative longevity based on alternative settings of one or more programmable parameters. For instance, the longevity may be estimated using fewer physiological sensor channels. Using the example of a three axis accelerometer, if two or all three axes have been selected for generating acceleration signals for detecting atrial systolic events during an atrial tracking ventricular pacing mode, the processor may determine an alternative sensor operation current drain that eliminates current drain for one accelerometer axis based on an alternative programming of the sensing control parameters that selects one fewer axis for sensing atrial systolic events. When three axes have been selected for sensing atrial systolic events, for instance, the alternative longevity may be determined by summing the current drain required for generating accelerometer vector signals from only two accelerometer axes instead of all three accelerometer axes using the cumulative operation time stored in memory 210 for only the two axes.

In another example, the processor may determine the alternative longevity based on changing an operating mode of the medical device. For example, if the operating mode is programmed to be a permanent atrial tracking ventricular pacing mode with automatic switching to a temporary non-tracking ventricular pacing mode, the alternative longevity may be determined based on reprogramming the permanent pacing mode to the non-tracking ventricular pacing mode. In this case, the alternative longevity may be determined by eliminating the processing burden current drain determined based on the accumulated time spent in the atrial tracking ventricular pacing mode. By reprogramming to the non-tracking ventricular pacing mode, the functional life of the IMD 14 may be extended while still providing ventricular rate support.

In other examples, alternative values or settings of other programmable parameters, such as pacing pulse amplitude, pacing pulse width, pacing electrode selection (with a different pacing impedance), pacing lower rate, etc. that may be used to control therapy delivery may be substituted for the currently programmed values or settings for determining an alternative longevity. For instance, an alternative pacing control parameter may be used to retrieve a therapy delivery current drain value from a LUT to determine an alternative therapy delivery current drain than the current drain determined at block 602.

An alternative value or setting of any control parameter that is a programmable parameter and is taken into account in the dynamic portion of the total current drain determined for estimating longevity may be selected for use in determining an alternative longevity at block 604. The estimated longevity determined at block 602 is based on the historical operating data and currently programmed control parameters of the medical device. The alternative longevity determined at block 604 is based on at least one change in a programmable control parameter that would alter the total current drain required for sensor operation, processing of a physiological signal during a specified operating mode, and/or therapy delivery. One or more alternative longevities may be determined at block 604, each based on an alternative value or setting for one or more programmable control parameters.

At block 606, a comparative longevity output is generated by the medical device system 10. For example, the estimated longevity may be determined by control circuit 206 and transmitted to external device 20 via telemetry circuit 208 (in FIG. 3). The one or more alternative longevities may be determined by processor 52 of external device 20. At block 606, processor 52 of external device 20 may cause the display unit 54 to generate a display of the estimated longevity based on historical data and currently programmed parameters and the one or more alternative longevities.

Figure 9:
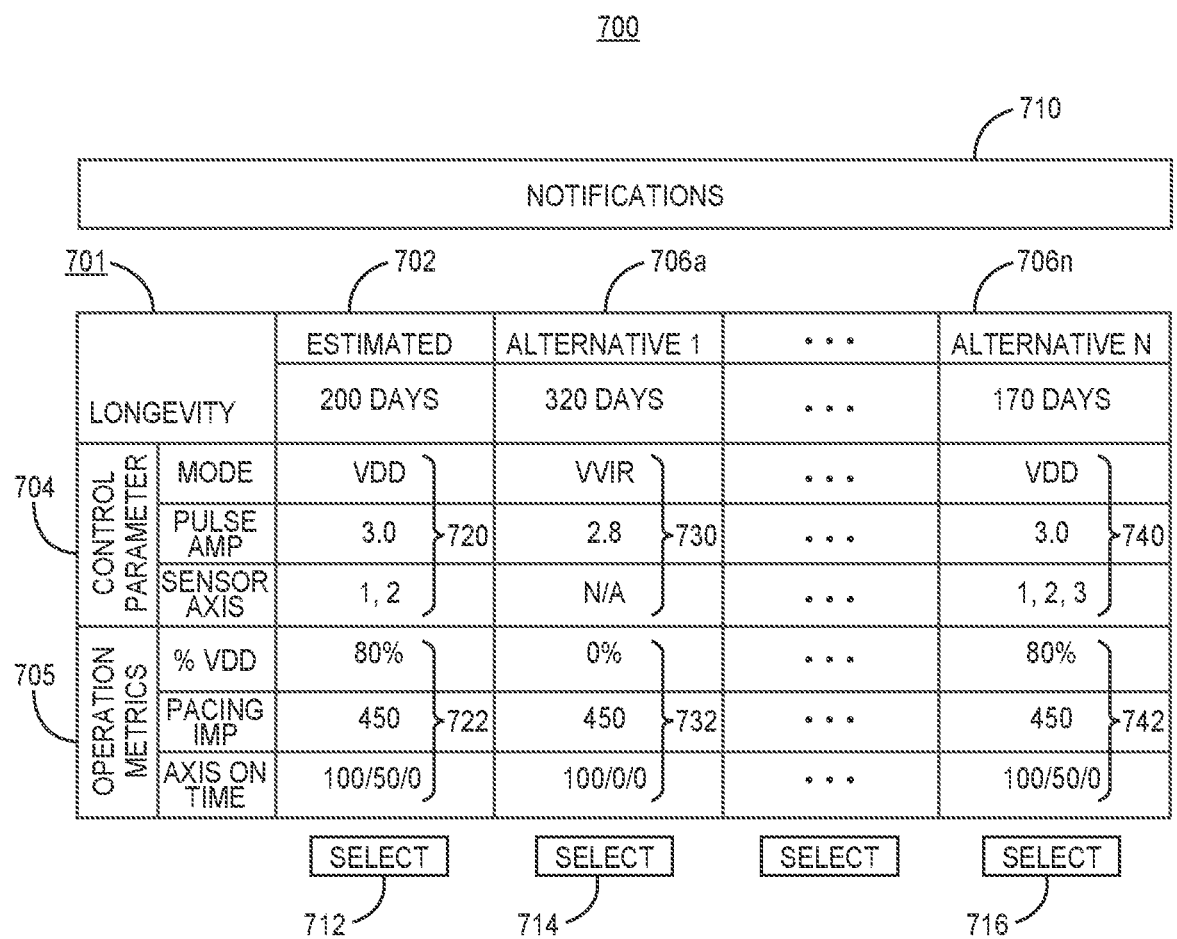
FIG. 9 is a diagram of one example of a graphical user interface that may be generated by a medical device system for displaying estimated longevity information to a user.

FIG. 9 is a diagram of a graphical user interface (GUI) 700 including data that may be output by one or more processors of medical device system 10 for displaying estimated longevity and related data. Processor 22 of external device 20 may generate data output for display in the GUI 700 by display unit 54. In one example, a notification window 710 is displayed including any statements or notifications relating to the estimated longevity. For example, the estimated longevity in days (which may be the adjusted estimated longevity determined at block 368 of FIG. 5) may be reported in notification window 710. Additionally or alternatively, a measured power source voltage may be reported. When a threshold voltage or threshold number of days has been reached, the notification window 710 may report a notification indicating that a replacement time or voltage or EOS has been reached.

GUI 700 may further include a table 701 of data relating to the reported estimated longevity. Table 701 may include the estimated longevity 702, shown in days in the example of FIG. 9. The estimated longevity 702 is determined using the techniques described above based on the actual historical operation data accumulated in IMD memory 210 and currently programmed control parameters. Programmable control parameters 704 associated with the estimated longevity 702 may be listed according to their actual current values or settings that contribute to or influence the total current drain determination used in determining the estimated longevity 702. Control parameters 704 that may be listed may include programmable therapy control parameters (such as pulse amplitude, pulse width, and lower pacing rate). Control parameters 704 may further include programmable sensing control parameters such as physiological sensor selection parameters. In the example of IMD 14 having a three axis accelerometer, the axes selected for detecting atrial systolic events may be displayed. Control parameters 704 may further include a programmable operating mode, such as the programmable therapy delivery mode and/or a programmable sensing or monitoring mode.

In the illustrative example shown, the listed values 720 of control parameters 704 used to determine estimated longevity 702 include a permanent VDD pacing mode (which may be switched temporarily to other pacing modes according to pacing mode switching criteria applied by control circuit 206). Other programmable control parameters that the estimated longevity 702 is based upon are shown to include a programmed pulse amplitude of 3.0 volts, and accelerometer axes 1 and 2 selected for producing acceleration vector signals for detecting atrial systolic events during the VDD pacing mode. It is to be understood that the particular control parameters and values listed in table 701 are illustrative in nature and not intended to be limiting. It is recognized that table 701 may list more than or less than three programmable control parameters that contribute to or influence the dynamic portion of the total current drain determined for estimating the longevity 702.

Longevity table 701 may further include a listing of operation metrics 705 that the control circuit 206 determines and stores in memory 210 for use in determining the estimated longevity 702. The operation metrics 705 listed in table 701 may be operation metrics that influence or contribute to the total current drain determined for estimating the longevity 702. For example, the operation metrics 705 associated with estimating longevity may include the percentage of time that IMD 14 operated in the VDD pacing mode, the measured pacing impedance, and the total "on" time of each accelerometer axis. The operation metrics 705 may be non-programmable values but are values that are measured or accumulated and stored in memory 210 of IMD 14 for use in determining the dynamic portions of the total current drain, used in determining the estimated longevity 702, e.g., the processing burden current drain (associated with the percentage of time in the VDD pacing mode), the sensor operation current drain (associated with the "on" time of each accelerometer axis), and the therapy delivery current drain (associated with the pacing impedance).

In the illustrative example, the values 722 of the operation metrics 705 displayed in GUI 700 include the percentage of time spent in the VDD pacing mode, the pacing impedance, and the percentage of accumulated time that each accelerometer axis is powered on. The percentage of time spent in the VDD pacing mode contributes to the processing burden current drain due to atrial systolic event detection and is determined by control circuit 206 to be 80%. The pacing impedance is measured as 450 ohms. The pacing impedance contributes the therapy delivery current drain. The "on" time of each accelerometer axis contributes to the sensor operation current drain. The first accelerometer axis is powered on 100% of the time and may be used for both atrial systolic event sensing and monitoring patient physical activity. The second accelerometer axis may be powered on 50% of the time, only during VDD pacing during which the accelerometer axis may be powered down some of the time due to blanking periods, which may be applied during each cardiac cycle. The third accelerometer axis may be a non-selected axis, being powered on 0% of the time as shown in the displayed values 722 of operation metrics 705.

The particular operation metrics 705 shown as examples in FIG. 9 are illustrative in nature. It is recognized that more than or fewer than three operation metrics may be displayed in table 701. Each of the operation metrics shown may be selected for display because each operation metric influences or contributes to the dynamic portion of the total current drain used to determine the estimated longevity 702.

The GUI 700 enables a user to view the estimated longevity 702 and one or more alternative longevities 706a-706n determined based on alternative settings 730, 740 of one or more programmable control parameters 704. Processor 52 of external device 20 may be configured to determine alternative longevities 706 according to adjusted values of one or more programmable control parameters 704 instead of the actual, programmed parameter values 720 associated with estimated longevity 702. In some examples, an alternative control parameter setting is selected automatically by processor 52. Additionally or alternatively, the alternative setting or value of a programmable control parameter may be entered manually by a user interacting with the graphical user interface.

The list of the control parameter settings 720 and operation metric values 722 corresponding to the estimated longevity 702 may be fixed in the displayed output table 701 because these settings and values represent the current settings and values of the programmable control parameters and historical operation metrics used for the estimated longevity 702 determination. However, the values 730, 740 of the control parameters 704 listed in association with one or more alternative longevities 706a, 706n may be adjustable by processor 52 or by a user. For example, a user interacting with GUI 700 may adjust one or more control parameter settings 730 listed for alternative longevity 706a. Processor 52 of external device 20 may determine the alternative longevity 706a based on the adjusted control parameter settings 730 by re-determining a total current drain based on the adjusted control parameter(s).

In this hypothetical example, a user may select an alternative permanent pacing mode of VVIR and a pacing pulse amplitude of 2.8 volts. The selected accelerometer axes may be indicated as non-applicable (N/A) since atrial systolic event sensing is not performed during the permanent VVIR pacing mode. Based on these alternative control parameter settings 730, processor 52 may determine expected or relative changes in the operation metrics 705. For example, if the pacing mode is changed to VVIR, the percentage of time spent in the VDD pacing mode may be 0%. The pacing impedance may remain the same at 450 ohms in this example. Since the accelerometer axes selected for atrial systolic event detection are not used during VVIR pacing, the expected axis "on" times may be 100% for the first axis used for monitoring patient physical activity and zero for the remaining two axes.

Processor 52 re-determines the sensor operation current drain, the processing burden current drain, and the therapy delivery current drain based on the alternative control parameter settings 730 and estimated operation metrics 732. The alternative longevity 706a is determined by processor 52 based on the re-determined total current drain. In this hypothetical example, the alternative control parameter settings may result in an increased alternative longevity of 320 days compared to the 200 days of estimated longevity 702. The alternative longevity may be determined based on the power source capacity at the reference voltage, e.g., at the pre-RRT voltage, and adjusted by the value of the elapsed time counter as described above in conjunction with FIG. 5.

In another illustrative example, an alternative longevity 706n may be determined by processor 52 based on a pacing mode of VDD, pulse amplitude 3.0 volts and all three accelerometer axes selected for sensing atrial systolic events for a longevity comparison to using only two accelerometer axes as associated with the estimated longevity 702. In this case, the percentage of operating in VDD pacing mode listed in operation metric values 742 may be estimated to be the same as the measured percentage listed in operation metric values 722 for the actual estimated longevity 702. The measured pacing impedance is the same at 450 ohms. The axis "on" times may be expected to be 100% for axis 1, 50% for axis 2 (the same as the actual axis 2 on time as listed in operation metric values 722), and 50% for axis 3, added for use in atrial systolic event sensing in the alternative control parameter settings 740. Processor 52 may determine a relatively shorter alternative longevity 706*n* of 170 days due to selection of the third accelerometer axis for atrial event detection compared to the estimated longevity 702 of 200 days when only two accelerometer axes are used for atrial event detection.

These illustrative examples are shown to demonstrate that the techniques disclosed herein for estimating the time between two voltages of a medical device power source may be based on actual programmed control parameter settings and historical operation metrics or alternative control parameter settings and assumed operation metrics based on the alternative control parameter settings. In this way, the estimated longevity 702 based on actual control parameter setting and historical operation metrics may be compared to one or more alternative longevities that can be expected if a programming change is made to one or more control parameters, which may include sensing and/or therapy delivery control parameters. Further, it is to be understood that alternative longevities 706*a*-706*n* may be determined and compared without determining estimated longevity 702. For example, alternative longevities 706*a*-706*n* may be determined at the time of IMD implantation, or anytime thereafter, based on various selections of programmable control parameters 704 and estimated or assumed values of operation metrics 705 as required for determining the total current drain and alternative longevities 706*a*-706*n*. When determining estimated longevity 702 or alternative longevities 706*a-n* at the time of IMD implantation, the first voltage may be the BOS voltage corresponding to 100% power source capacity and the second, lower voltage may be any selected voltage associated with a second, lower power source capacity, such as the EOS voltage and 0% capacity.

The GUI 700 displayed by display unit 54 may include a "select" button 712, 714 and 716 for each of the listings of control parameter values 720, 730 and 740 associated with the respective estimated longevity 702 and alternative longevities 706*a* and 706*n*. A user may select the existing control parameter values 720 using select button 712. External device 20 does not make any programming changes to the control parameters 704 since this selection corresponds to the existing programmed control parameter values.

However, a user may select alternative control parameter settings 730 or 740 based on the alternative longevity 706*a* or 706*n* with an understanding of how the operation metric values 732 and 742 are expected to change the expected longevity. Various trade-offs may be made between therapy delivery and/or physiological signal monitoring operations and power source longevity. For example, expected improvements in therapy delivery based on more accurate atrial event sensing based on all three sensing vectors may be selected using select button 716 when the alternative longevity 706*n* is within an acceptable range of the estimated longevity 702. On the other hand, control parameter values 730 may be selected by using select button 714 in order to maximize the longevity while providing the patient with basic ventricular rate support in the VVIR pacing mode as listed in control parameter settings 730.

In response to a select button 714 or 716 associated with an alternative longevity 706*a* or 706*n* being selected by a user, external device processor 52 may control telemetry unit 58 to transmit the corresponding programmable control parameter settings 730 or 740 (or at least any settings that represent a change from current settings 720) to IMD 14. In this way, a user may adjust one or more programmable control parameters 704 in the GUI 700 to observe how changes in programmable control parameters change the expected, alternative longevity 706*a*-706*n* compared to the actual, estimated longevity 702. Using a select button 714 or 716 the user may input programming changes to multiple programmable control parameters simultaneously based on the comparative display of the estimated and alternative longevity values 702, 706*a*-706*n*.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or modules associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPLAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device system has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device system comprising:
a power source;
a therapy delivery circuit configured to deliver electrical stimulation pulses;
a sensor coupled to the power source and configured to generate a physiological signal;
a control circuit coupled to the power source, the therapy delivery circuit and the sensor, the control circuit configured to:
detect events from the physiological signal;
control the therapy delivery circuit to deliver the electrical stimulation pulses based on at least the events detected from the physiological signal; and
determine a voltage of the power source; and
a processor configured to:
determine a first current drain including electrical current required from the power source for at least one of generating the physiological signal and detecting the events from the physiological signal;
determine that the determined voltage of the power source has reached a first voltage;
start a timer to track an elapsed time in response to determining that the determined voltage of the power source has reached the first voltage;
determine an estimated time from the first voltage of the power source until a second voltage of the power source based on the first current drain and a power source capacity difference, where the first voltage of the power source corresponds to a first power source capacity, the second voltage corresponds to a second power source capacity less than the first power source capacity, and the power source capacity difference is the difference between the first power source capacity and the second power source capacity;
determine a value of the timer when the estimated time is determined;
adjust the estimated time by the value of the timer; and
generate an output based on the adjusted estimated time; and
a memory configured to store data corresponding to the adjusted estimated time in response to the output generated by the processor.

2. The medical device system of claim 1, wherein the processor is configured to:
determine that the adjusted estimated time has reached a threshold longevity; and
generate the output by generating a notification in response to the adjusted estimated time reaching the threshold longevity.

3. The medical device system of claim 1, wherein the control circuit is configured to:
determine an accumulated time of powering the sensor for generating the physiological signal; and
determine the first current drain based on at least the accumulated time of powering the sensor for generating the physiological signal.

4. The medical device of claim 1, wherein:
the control circuit is configured to:
switch between a first operating mode that includes detecting the events from the physiological signal and a second operating mode that does not include detecting the events from the physiological signal; and
determine an accumulated time of operating in the first operating mode; and the processor is configured to determine the first current drain based on at least the accumulated time of operating in the first operating mode.

5. The medical device system of claim 1, wherein the processor is configured to determine the first current drain by determining at least a processing burden current drain corresponding to electrical current from the power source required by the control circuit for detecting the events from the physiological signal.

6. The medical device system of claim 1, wherein the therapy delivery circuit is configured to deliver the electrical stimulation pulses according to a therapy;
wherein the processor is further configured to determine the first current drain by determining a therapy delivery current drain from the power source required for delivering the therapy.

7. The medical device system of claim 6, wherein the control circuit is configured to determine the therapy delivery current drain by:
determining a pacing impedance;
determining a pacing current drain based on at least the pacing impedance;
determining a pacing frequency; and
determining the therapy delivery current drain based on the pacing current drain and the pacing frequency.

8. The medical device system of claim 7, further comprising:
a memory storing at least one look up table including a plurality of pacing current drain values corresponding to a plurality of pacing control parameter values;
wherein the control circuit is configured to determine the therapy delivery current drain by selecting a pacing current drain value from the look up table.

9. The medical device system of claim 1, wherein:
the sensor includes a plurality of channels, each channel of the plurality of channels configured to generate a channel signal when selectively powered by the power source; and
the control circuit is configured to determine the first current drain by:
for each channel of the plurality of channels, determining an accumulated time that the channel is selectively powered by the power source to generate the channel signal; and
determining the first current drain based on the determined accumulated time that each channel of the sensor is selectively powered by the power source.

10. The medical device system of claim 1, wherein:
the processor is further configured to:
determine the first current drain and the estimated time until the second voltage in response to determining that the determined voltage of the power source has reached the first voltage.

11. The medical device system of claim 1, wherein the processor is configured to:
determine the first current drain based on a current setting of a control parameter;
determine a second current drain based on an alternative setting of the control parameter;
determine an alternative time from the first voltage of the power source until the second voltage of the power source based on the second current drain and the power source capacity difference; and
generate a comparative output of the estimated time and the alternative time.

12. The medical device system of claim 1, further comprising a display unit configured to display a graphical user interface in response to the generated output, the graphical user interface comprising at least a display representative of the estimated time.

13. The medical device system of claim 1, wherein:
the sensor comprises an accelerometer having a plurality of axes, wherein each axis of the accelerometer is configured to generate an acceleration signal along a direction of the axis, the sensor configured to generate the physiological signal comprising an acceleration signal from at least one of the plurality of axes;
the control circuit is further configured to detect a cardiac event from the physiological signal;
the therapy delivery circuit further configured to deliver the electrical stimulation pulses by generating a pacing pulse in response to a cardiac event detected from the physiological signal; and
the processor is configured to determine the first current drain by:
determining a sensor operation current drain by determining an accumulated time of selectively powering each axis of the plurality of axes of the accelerometer for generating the physiological signal;
determining a processing burden current drain required for detecting the cardiac events from the physiological signal; and
determining a therapy delivery current drain by:
determining a pacing impedance;
determining at least one pacing pulse control parameter;
determining a pacing frequency; and
determining the therapy delivery current drain based on the pacing impedance, the at least one pacing pulse control parameter and the pacing frequency; and
determining the first current drain based on at least the sensor operation current drain, the processing burden current drain and the therapy delivery current drain.

14. A method comprising:
generating a physiological signal by a sensor coupled to a power source;
detecting events from the physiological signal;
delivering electrical stimulation pulses based on at least the events detected from the physiological signal;
determining a voltage of the power source;
determining a first current drain including electrical current required from the power source for at least one of: generating the physiological signal and detecting the events from the physiological signal;
determining that the determined voltage of the power source has reached a first voltage;
starting a timer to track an elapsed time in response to determining that the determined voltage of the power source has reached the first voltage;
determining an estimated time from a first voltage of the power source until a second voltage of the power source based on the first current drain and a power source capacity difference, where the first voltage of the power source corresponds to a first power source capacity, the second voltage corresponds to a second power source capacity less than the first power source capacity, and the power source capacity difference is the difference between the first power source capacity and the second power source capacity;
determining a value of the timer when the estimated time is determined;
adjusting the estimated time by the value of the timer; and
generating an output based on the adjusted estimated time; and
storing in memory data corresponding to the adjusted estimated time in response to the generated output.

15. The method of claim 14, comprising:
determining that the adjusted estimated time has reached a threshold longevity; and
generating the output by generating a notification in response to the adjusted estimated time reaching the threshold longevity.

16. The method of claim 14, comprising:
determining an accumulated time of powering the sensor for generating the physiological signal; and
determining the first current drain based on at least the accumulated time of powering the sensor for generating the physiological signal.

17. The method of claim 14, comprising:
switching between a first operating mode that includes detecting the events from the physiological signal and a second operating mode that does not include detecting the events from the physiological signal;
determining an accumulated time of operating in the first operating mode; and
determining the first current drain based on at least the accumulated time of operating in the first operating mode.

18. The method of claim 14, comprising determining the first current drain by determining at least a processing burden current drain corresponding to electrical current from the power source required for detecting the events from the physiological signal.

19. The method of claim 14, further comprising:
delivering the electrical stimulation pulses according to a therapy; and
determining the first current drain by determining a therapy delivery current drain from the power source required for delivering the therapy.

20. The method of claim 19, wherein the control circuit is configured to determine the therapy delivery current drain by:
determining a pacing impedance;
determining a pacing current drain based on at least the pacing impedance;
determining a pacing frequency; and
determining the therapy delivery current drain based on the pacing current drain and the pacing frequency.

21. The method of claim 20, further comprising:
storing at least one look up table including a plurality of pacing current drain values corresponding to a plurality of pacing control parameter values;
wherein determining the therapy delivery current drain comprises selecting a pacing current drain value from the look up table.

22. The method of claim 14, comprising:
generating a channel signal by each channel of a plurality of channels of the sensor when the channel is selectively powered by the power source; and
determining the first current drain by:
for each channel of the plurality of channels, determining an accumulated time that the channel is selectively powered by the power source to generate the channel signal; and
determining the first current drain based on the determined accumulated time that each channel of the sensor is selectively powered by the power source.

23. The method of claim 14, comprising:
determining the first current drain and the estimated time until the second voltage in response to determining that the determined voltage of the power source has reached the first voltage.

24. The method of claim 14, comprising:
determining the first current drain based on a current setting of a control parameter;
determining a second current drain based on an alternative setting of the control parameter;
determining an alternative estimated time from the first voltage of the power source until the second voltage of the power source based on the second current drain and the power source capacity difference; and
generating a comparative output of the estimated time and the alternative estimated time.

25. The method of claim 14, comprising displaying a graphical user interface in response to the generated output, the graphical user interface comprising at least a display representative of the estimated time.

26. The method of claim 14, comprising:
generating the physiological signal by generating an acceleration signal from at least one axis of an accelerometer having a plurality of axes;
detecting cardiac events from the physiological signal;
delivering the electrical stimulation pulses by generating a pacing pulse in response to a cardiac event detected from the physiological signal; and
determining the first current drain by:
determining a sensor operation current drain by determining an accumulated time of selectively powering each axis of the plurality of axes of the accelerometer for generating the physiological signal;
determining a processing burden current drain required for detecting the cardiac events from the physiological signal; and
determining a therapy delivery current drain by:
determining a pacing impedance;
determining at least one pacing pulse control parameter;
determining a pacing frequency; and
determining the therapy delivery current drain based on the pacing impedance, the at least one pacing pulse control parameter and the pacing frequency; and
determining the first current drain based on at least the sensor operation current drain, the processing burden current drain and the therapy delivery current drain.

27. A non-transitory computer readable medium storing a set of instructions that, when executed by processing circuitry of a medical device system, cause the medical device system to:
generate a physiological signal by a sensor coupled to a power source;
detect events from the physiological signal;
deliver electrical stimulation pulses based on at least the events detected from the physiological signal;
determine a voltage of the power source;
determine a current drain including electrical current required from the power source for at least one of: generating the physiological signal and detecting the events from the physiological signal;
determine that the determined voltage of the power source has reached a first voltage;
start a timer to track an elapsed time in response to determining that the determined voltage of the power source has reached the first voltage;
determine an estimated time from a first voltage of the power source until a second voltage of the power source based on the first current drain and a power source capacity difference, where the first voltage of the power source corresponds to a first power source capacity, the second voltage corresponds to a second power source capacity less than the first power source capacity, and the power source capacity difference is the difference between the first power source capacity and the second power source capacity;
determine a value of the timer when the estimated time is determined;
adjust the estimated time by the value of the timer;
generate an output based on the adjusted estimated time; and
store data corresponding to the adjusted estimated time in response to the generated output.

* * * * *